United States Patent
Montgomery et al.

(10) Patent No.: US 12,336,998 B2
(45) Date of Patent: *Jun. 24, 2025

(54) JAK1 PATHWAY INHIBITORS FOR THE TREATMENT OF CYTOKINE-RELATED DISORDERS

(71) Applicant: Incyte Corporation, Wilmington, DE (US)

(72) Inventors: Michael O'Neill Montgomery, Yardley, PA (US); Ahmad Naim, Hatboro, PA (US); Susan Snodgrass, Greenville, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/382,939

(22) Filed: Oct. 23, 2023

(65) Prior Publication Data

US 2024/0156818 A1  May 16, 2024

Related U.S. Application Data

(63) Continuation of application No. 17/379,336, filed on Jul. 19, 2021, now Pat. No. 11,833,152, which is a continuation of application No. 16/276,157, filed on Feb. 14, 2019, now Pat. No. 11,103,510.

(60) Provisional application No. 62/631,825, filed on Feb. 18, 2018, provisional application No. 62/710,446, filed on Feb. 16, 2018.

(51) Int. Cl.
| | |
|---|---|
| A61K 31/397 | (2006.01) |
| A61K 31/4155 | (2006.01) |
| A61K 31/437 | (2006.01) |
| A61K 31/4427 | (2006.01) |
| A61K 31/519 | (2006.01) |
| A61K 31/56 | (2006.01) |
| A61K 31/573 | (2006.01) |
| A61P 37/00 | (2006.01) |
| A61P 37/02 | (2006.01) |
| C07K 16/28 | (2006.01) |

(52) U.S. Cl.
CPC ........ *A61K 31/519* (2013.01); *A61K 31/4155* (2013.01); *A61K 31/437* (2013.01); *A61K 31/573* (2013.01); *A61P 37/00* (2018.01); *A61P 37/02* (2018.01); *C07K 16/2866* (2013.01)

(58) Field of Classification Search
CPC ... A61K 31/397; A61K 31/4427; A61K 31/56
USPC .......... 514/171, 210.2, 210.21, 338
See application file for complete search history.

(56) References Cited

U.S. PATENT DOCUMENTS

| | | |
|---|---|---|
| 5,521,184 A | 5/1996 | Zimmerman |
| 7,335,667 B2 | 2/2008 | Rodgers et al. |
| 7,598,257 B2 | 10/2009 | Rodgers et al. |
| 7,834,022 B2 | 11/2010 | Rodgers et al. |
| 8,158,616 B2 | 4/2012 | Rodgers et al. |
| 8,309,718 B2 | 11/2012 | Li et al. |
| 8,410,265 B2 | 4/2013 | Zhou et al. |
| 8,415,362 B2 | 4/2013 | Rodgers et al. |
| 8,486,902 B2 | 7/2013 | Rodgers et al. |
| 8,513,270 B2 | 8/2013 | Arvanitis et al. |
| 8,563,541 B2 | 10/2013 | Arvanitis et al. |
| 8,604,043 B2 | 12/2013 | Li et al. |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,765,734 B2 | 7/2014 | Huang et al. |
| 8,933,085 B2 | 1/2015 | Rodgers et al. |
| 8,987,443 B2 | 3/2015 | Liu et al. |
| 9,034,884 B2 | 5/2015 | Rodgers et al. |
| 9,181,271 B2 | 11/2015 | Li et al. |
| 9,193,733 B2 | 11/2015 | Rodgers et al. |
| 9,249,145 B2 | 2/2016 | Rodgers et al. |
| 9,358,229 B2 | 6/2016 | Vannucchi et al. |
| 9,359,358 B2 | 6/2016 | Rodgers et al. |
| 9,382,231 B2 | 7/2016 | Li et al. |
| 9,487,521 B2 | 11/2016 | Zhou et al. |
| 9,498,467 B2 | 11/2016 | Leopold et al. |
| 9,549,916 B2 | 1/2017 | Fu et al. |
| 9,655,854 B2 | 5/2017 | Yeleswaram et al. |
| 9,802,957 B2 | 10/2017 | Zhou et al. |
| 9,926,301 B2 | 3/2018 | Li et al. |
| 9,926,601 B2 | 3/2018 | Gertler et al. |
| 9,993,480 B2 | 6/2018 | Vannucchi et al. |
| 10,166,191 B2 | 1/2019 | Ni et al. |
| 10,435,392 B2 | 10/2019 | Li et al. |
| 11,001,571 B2 | 5/2021 | Li et al. |
| 11,103,510 B2 | 8/2021 | Montgomery et al. |

(Continued)

FOREIGN PATENT DOCUMENTS

| | | |
|---|---|---|
| CN | 101910152 | 12/2010 |
| CN | 102026999 | 4/2011 |

(Continued)

OTHER PUBLICATIONS

Malaysian Office Action in Malaysian Application No. PI2020004197, dated Apr. 29, 2024, 4 pages.
Aikawa, "Cytokine storm in the pathogenesis of multiple organ dysfunction syndrome associated with surgical insults," Nihon Geka Gakkai Zasshi, Sep. 1996, 97(9):771-777 (English abstract only).

(Continued)

*Primary Examiner* — Raymond J Henley, III
(74) *Attorney, Agent, or Firm* — Fish & Richardson P.C.

(57) ABSTRACT

This disclosure relates to JAK1 pathway inhibitors and the use thereof in treating cytokine-related diseases or disorders such as cytokine release syndrome (CRS), hemophagocytic lymphohistiocytosis (HLH), macrophage activation syndrome (MAS), and CAR-T-cell-related encephalopathy syndrome (CRES).

24 Claims, 8 Drawing Sheets

(56) References Cited

U.S. PATENT DOCUMENTS

| | | |
|---|---|---|
| 11,304,949 B2 | 4/2022 | Howell et al. |
| 11,591,318 B2 | 2/2023 | Li et al. |
| 11,833,152 B2 | 12/2023 | Montgomery et al. |
| 11,905,275 B2 | 2/2024 | Li et al. |
| 11,957,661 B2 | 4/2024 | Smith et al. |
| 2006/0106020 A1 | 5/2006 | Rodgers et al. |
| 2006/0183906 A1 | 8/2006 | Rodgers et al. |
| 2007/0135461 A1 | 6/2007 | Rodgers et al. |
| 2008/0312258 A1 | 12/2008 | Rodgers et al. |
| 2008/0312259 A1 | 12/2008 | Rodgers et al. |
| 2009/0233903 A1 | 9/2009 | Rodgers et al. |
| 2009/0318405 A1 | 12/2009 | Li et al. |
| 2010/0113416 A1 | 5/2010 | Friedman et al. |
| 2010/0298334 A1 | 11/2010 | Rodgers et al. |
| 2010/0298355 A1 | 11/2010 | Li et al. |
| 2011/0059951 A1 | 3/2011 | Rodgers et al. |
| 2011/0086810 A1 | 4/2011 | Rodgers et al. |
| 2011/0207754 A1 | 8/2011 | Li et al. |
| 2011/0224190 A1 | 9/2011 | Huang et al. |
| 2011/0288107 A1 | 11/2011 | Parikh et al. |
| 2012/0014968 A1 | 1/2012 | Walsh et al. |
| 2012/0149681 A1 | 6/2012 | Rodgers et al. |
| 2012/0149682 A1 | 6/2012 | Rodgers et al. |
| 2013/0018034 A1 | 1/2013 | Yao et al. |
| 2013/0045963 A1 | 2/2013 | Rodgers et al. |
| 2013/0060026 A1 | 3/2013 | Zhou et al. |
| 2014/0005166 A1 | 1/2014 | Rodgers et al. |
| 2014/0121198 A1 | 5/2014 | Li et al. |
| 2014/0135350 A1 | 5/2014 | Ni et al. |
| 2014/0256941 A1 | 9/2014 | Liu et al. |
| 2014/0343030 A1 | 11/2014 | Li et al. |
| 2015/0065447 A1 | 3/2015 | Sandor |
| 2015/0065484 A1 | 3/2015 | Yeleswaram et al. |
| 2015/0087662 A1 | 3/2015 | Li et al. |
| 2015/0118229 A1 | 4/2015 | Voss et al. |
| 2015/0246046 A1 | 9/2015 | Vaddi |
| 2015/0342952 A1 | 12/2015 | Leopold et al. |
| 2015/0344497 A1 | 12/2015 | Zhou et al. |
| 2016/0289215 A1 | 10/2016 | Li et al. |
| 2018/0312492 A1 | 11/2018 | Li et al. |
| 2019/0060311 A1 | 2/2019 | Shanler et al. |
| 2019/0175578 A1 | 6/2019 | Koblish et al. |
| 2019/0233392 A1 | 8/2019 | Wang et al. |
| 2019/0255053 A1 | 8/2019 | Montgomery et al. |
| 2019/0328739 A1 | 10/2019 | Howell et al. |
| 2019/0331697 A1 | 10/2019 | Howell et al. |
| 2020/0010456 A1 | 1/2020 | Li et al. |
| 2020/0063188 A1 | 2/2020 | Howell et al. |
| 2021/0238168 A1 | 8/2021 | Li et al. |
| 2021/0380563 A1 | 12/2021 | Zhou et al. |
| 2022/0040187 A1 | 2/2022 | Montgomery et al. |
| 2022/0175731 A1 | 6/2022 | Smith et al. |
| 2022/0202834 A1 | 6/2022 | Smith et al. |
| 2022/0378746 A1 | 12/2022 | Smith et al. |
| 2023/0159501 A1 | 5/2023 | Li et al. |

FOREIGN PATENT DOCUMENTS

| | | |
|---|---|---|
| CN | 102985417 | 3/2013 |
| JP | 6415543 | 10/2018 |
| WO | WO 2000009495 | 2/2000 |
| WO | WO 2000053595 | 9/2000 |
| WO | WO 2001014402 | 3/2001 |
| WO | WO 2001064655 | 9/2001 |
| WO | WO 2002000196 | 1/2002 |
| WO | WO 2003024967 | 3/2003 |
| WO | WO 2003037347 | 5/2003 |
| WO | WO 2003099771 | 12/2003 |
| WO | WO 2004005281 | 1/2004 |
| WO | WO 2004046120 | 6/2004 |
| WO | WO 2004056786 | 7/2004 |
| WO | WO 2004080980 | 9/2004 |
| WO | WO 2005028444 | 3/2005 |
| WO | WO 2006056399 | 6/2006 |
| WO | WO 2009114512 | 9/2009 |
| WO | WO 2011130146 | 10/2011 |
| WO | WO 2012068450 | 5/2012 |
| WO | WO 2012076063 | 6/2012 |
| WO | WO 2012177606 | 12/2012 |
| WO | WO 2013036611 | 3/2013 |
| WO | WO 2013040863 | 3/2013 |
| WO | WO 2014184275 | 11/2014 |
| WO | WO 2014184327 | 11/2014 |
| WO | WO 2014184328 | 11/2014 |
| WO | WO 2014184350 | 11/2014 |
| WO | WO 2015184305 | 12/2015 |
| WO | WO 2017096331 | 6/2017 |
| WO | WO 2017165571 | 9/2017 |
| WO | WO 2018013918 | 1/2018 |
| WO | WO 2020191041 | 9/2020 |

OTHER PUBLICATIONS

Algre et al., "Hypothermia and hypoglycemia induced by anti-CD3 monoclonal antibody in mice: role of tumor necrosis factor," Eur. J. Immunol., 1990, 20(3):707-710.

Argentina Office Action in Argentina Application No. 20140101971, dated Nov. 22, 2019, 6 pages.

Australian Office Action in Australian Application No. 2018223058, dated Apr. 8, 2019, 4 pages.

Australian Office Action in Australian Application No. 2018223058, Dec. 17, 2019, 4 pages.

Australian Office Action in Australian Application No. 2019221667, dated Jan. 23, 2024, 6 pages.

Barabino et al., "Tear film and ocular surface tests in animal models of dry eye: uses and limitations," Experimental Eye Research, 2004, 79: 613-621.

Beck et al., "Brief Report: Alleviation of Systemic Manifestations of Castleman's Disease by Monoclonal Anti-Interleukin-6 Antibody," N. Engl. J. Med., 1994, 330(9): 602-605.

Bennett et al., "Proposals for the classification of the myelodysplastic syndromes," British Journal of Haematology, 1982, 51: 189-199.

Berge et al., "Pharmaceutical Salts," J. Pharma. Science, 1977, 66(1): 1-19.

Bhattacharya et al., "Brittain, ed. Polymorphism in Pharmaceutical Solids," 2009, p. 327-345.

Blom et al., "Optimizing Preparative LC/MS Configurations and Methods for Parallel Synthesis Purification," J. Comb. Chem., 2003, 5: 670-683.

Blom et al., "Preparative LC-MS Purification: Improved Compound-Specific Method Optimization," J. Comb. Chem., 2004, 6: 874-883.

Blom, "Two-Pump at-Column-Dilution Configuration for Preparative Liquid Chormatography—Mass Spectrometry," J. Comb. Chem., 2002, 4: 295-301.

Bock et al. "Managing drug resistance in cancer: lessons from HIV therapy." Nature, Jul. 2012, vol. 12, pp. 494-501.

Bolen, "Nonreceptor tyrosine protein kinases", Oncogene, 1993, 8(8):2025-31.

Bollrath et al., "gp130-Meidated Stat3 Activation in Enterocytes Regulates Cell Survival and Cell-Cycle Progression during Colitis-Associated Tumorigenesis," Cancer Cell, 15: 91-102 (2009).

Borgia et al., "Features, Treatment, and Outcomes of Macrophage Activation Syndrome in Childhood-Onset Systemic Lupus Erythematosus," Arthritis Rheumatol., 2018, 70(4):616-624.

Borie et al., "Combined Use of the Jak3 Inhibitor CP-690, 550 with Mycophenolate Mofetil to Prevent Kidney Allograft Rejection in Nonhuman Primates," Transplantation, Dec. 2005, 80(12): 1756-64.

Bosworth, "JAK1/JAK2 Inhibitor Ruxolitinib Is a Rising Start," Clinical Oncology, Apr. 2011, 06:04, 3 pages.

Boudny, et al., "JAK/STAT signaling pathways and cancer", Neoplasm, 49:349-355, 2002.

Bowman, et al. "STATs in oncogenesis", Oncogene, 19:2474-2488, 2000.

Brentjens et al., "Treatment of chronic lymphocytic leukemia with genetically targeted autologous T cells: case report of an unforeseen adverse event in a phase I clinical trial," Mol Ther, 2010, 18:666-668.

(56) References Cited

OTHER PUBLICATIONS

Broglie et al., "Ruxolitinib for treatment of refractory hemophagocytic lymphohistiocytosis," blood advances, Aug. 22, 2017, 1(19):1533-1536.
Bromberg et al., "Inflammation and Cancer: IL-6 and Sta T3 Complete the Link," Cancer Cell, 15 :79-80 (2009).
Brunning et al., "Myelodysplastic syndromes/neoplasms" in Chapter 5, Swerdlow, et al., eds. WHO Classification of Tumours of Haematopoietic and Lymphoid Tissues. (ed. 4th edition): Lyon, France: IARC Press, 2008, 4$^{th}$ edition, pp. 88-103.
Bugelski et al., "Monoclonal antibody-induced cytokine-release syndrome," Expert Review of Clinical Immunology, 2009, 5(5):499-521.
Burdeinick-Kerr et al., "Noncytolytic Clearance of Sindbis Virus Infection from Neurons by Gamma Interferon Is Dependent on Jak/Stat Signaling," Journal of Virology, Apr. 2009, 83(8):3429-3435.
Burger et al., "Janus kinase inhibitor INCB20 has antiproliferative and apoptotic effects on human myeloma cells in vitro and in vivo," Mol. Cancer Ther., 2009, 8(1):26-35.
Burger, et al., "Gp130 and ras mediated signaling in human plasma cell line IN/a-6: a cytokine-regulated tumor model for plasmacytoma", Hematol J., 2:42-53, 2001.
Campas-Moya, "Ruxolitinib. Tyrosine-protein kinase JAK1/2 inhibitor, treatment of myelofibrosis, treatment of myeloproliferative neoplasms, treatment of psoriasis", Drugs of the Future, (Jun. 2010) vol. 35, No. 6, pp. 457-465.
Candotti et al., "Molecular aspects of primary immuno-deficiencies: lessons from cytokine and other signaling pathways.", J Clin Invest, 2002, 109(10):1261-9.
Candotti et al., "Structural and functional basis for JAK3-deficient severe combined immunodeficiency.", Blood, 1997, 90(10):3996-4003.
Cetkovic-Cvrlje et al., "Targeting JAK3 with JANEX-1 for prevention of autoimmune type 1 diabetes in NOD mice.", Clin Immunol, 2003, 106(3): 213-25.
Chalandon, "Targeting mutated protein tyrosine kinases and their signaling pathways in hematologic malignancies", Haematologica, 2005, 90 (7):949-68.
Changelian et al., "Prevention of Organ Allograft Rejection by a Specific Janus Kinase 3 Inhibitor", Science, 2003, 302:875-878.
Chari et al., "Complete Remission Achieved with Single Agent CNTO 328, an Anti-IL-6 Monoclonal Antibody, in Relapsed and Refractory Myeloma," Clinical Lymphoma, Myeloma & Leukemia, 2013, 13(3):333-337.
Chen et al., "Blockade of interleukin-6 signaling augments regulatory T-cell reconstitution and attenuates the severity of graft-versus-host disease," Blood, Jul. 2009, 114(4): 891-900.
Chen et al., "Rhinovirus Induces Airway Epithelial Gene Expression through Double- Stranded RNA and IFN-Dependent Pathways," Am J of Respir Cell and Mol Bio., Feb. 2006, 34(2):192-203.
Chen et al., "Stat3 Activation in Human Endometrial and Cervical Cancer", British Journal of Cancer, 2007, 96:591-599.
Chen et al., "Induction of myelodysplasia by myeloid-derived suppressor cells," J Clin Invest, Nov. 2013, 123(11): 4595-611.
Cheson et al., "Report of an international working group to standardize response criteria for myelodysplastic syndromes," Blood, Dec. 2000, 96(12): 3671-4.
Chilean Office Action in Chilean Application No. 202002102, dated Feb. 12, 2024, 4 pages (with English Translation).
Chinese Office Action in Chinese Application No. 201980024450.3, dated Aug. 24, 2023, 8 pages (with English Translation).
Choy et al., "Therapeutic Benefit of Blocking Interleukin-6 Activity With an Anti- Interleukin-6 Receptor Monoclonal Antibody in Rheumatoid Arthritis," Arthritis & Rheumatism, 2002, 46(12) 3143-3150.
Cilloni et al., "Emerging drugs for chronic myeloid leukemia", Expert Opinion on Emerging Drugs, Jun. 2010, 15(2):175-184.
Claessens et al., "In vitro proliferation and differentiation of erythyroid progenitors from patients with myelodysplastic syndromes: evidence for Fas-dependent apoptosis, " Blood, Mar. 2012, 1594-1601.
Clark et al., "Discovery and Development of Janus Kinase (JAK) inhibitors for Inflammatory Diseases," J Med Chem., 2014, pp. A-P.
Clinicaltrials.com, "A Study to Evaluate the Efficacy and Safety of INCB054707 in Participants With Vitiligo," NCT04818346, dated Jul. 21, 2022, 7 pages.
Coligan et al., "Current Protocols in Immunology," Wiley Press, vol. 3, 21 pages (Chapter Abstracts Only).
Conklyn et al., "The JAK3 inhibitor CP0690550 selectively reduces NK and CD8+ cell numbers in cynomolgus monkey blood following chronic oral dosing", Journal of Leukocyte Biology, 2004, 76:1248-1255.
Costa Rican Office Action in Costa Rican Application No. 2015-0633, dated Feb. 25, 2020, 13 pages.
Costa Rican Office Action in Costa Rican Application No. 2015-0633, dated Sep. 20, 2019, 14 pages.
Das et al., "Janus kinase inhibition lessens inflammation and ameliorates disease in murine models of hemophagocytic lymphohistiocytosis, " Blood, Jan. 29, 2016, 127(3):1666-1675.
De Vos et al., (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells.", Br J Haematol, 2000, 109(4): 823-8.
Desai et al., "Vitiligo: Oral and Topical JAKs Show Promise," Practical Dermatology, Jul. 2020, 30-31.
Deuse et al., "Novel Immunosuppression: R348, a JAK3- and Syk-Inhibitor Attenuates Acute Cardiac Allograft Rejection", Transplantation, 2008, 85(6) 885-892.
Dudley et al., "A VEGF/JAK2/STAT5 axis may partially mediate endothelial cell tolerance to hypoxia, " Biochem J, Sep. 2005, 390(Pt 2): 427-36.
Eghtedar, "Phase II Study of the JAK2 Inhibitor, INCB018424, in Patients with Refractory Leukemias Including Post-Myeloproliferative Disorder Acute Myeloid Leukemia", American Society of Hematology (ASH) annual meeting in Orlando, FL (Dec. 6, 2010), Abstract/poster 509.
Eurasian Office Action in Eurasian Application No. 201592199, dated Feb. 4, 2019, 7 pages.
European Office Action in European Application No. 19707655.7, dated Jun. 26, 2023, 6 pages.
European Search Report in European Application No. 18215671.1, dated May 14, 2019, 5 pages.
Fayad et al., "Interleukin-6 and interleukin-10 levels in chronic lymphocytic leukemia: correlation with phenotypic characteristics and outcome," Blood, Jan. 2001, 97(1): 256-263.
Fenaux et al., "A randomized phase 3 study of lenalidomide versus placebo in RBC transfusion-dependent patients with Low-/Intermediate-1-risk myelodysplastic syndromes with del5g," Blood, Oct. 2011, 118(14): 3765-76.
Fenaux, et al., "Efficacy of azacitidine compared with that of conventional care regimens in the treatment of higher-risk myelodysplastic syndromes: a randomised, open-label, phase III study," Lancet Oncol, Mar. 2009, 10: 223-32.
Ferran et al., "Cytokine-related syndrome following injection of anti-CD3 monoclonal antibody: further evidence for transient in vivo T cell activation," Eur. J. Immunol., 1990, 20(3):509-515.
Ferran et al., "Inter-mouse strain differences in the in vivo anti-CD3 induced cytokine release," Clin. Exp. Immunol., 1991, 86(3):537-543.
Fiskus et al., "Synergistic Activity of Combinations of JAK2 Kinase Inhibitor with PI3K/mTOR, MEK or PIM Kinase Inhibitor Against Human Myeloproliferative Neoplasm Cells Expressing JAK2V617F" J. American Chem. Soc., 52nd Annual Meeting of the American-Society-of-Hematology (ASH); Orlando, FL, USA; Dec. 4-7, 2010, ACS Publications, Nov. 1, 2010, 116(21):349, XP002667216, ISSN: 0002-7863 (1 page).
Flex et al., "Somatically acquired JAK1 mutations in adult acute lymphoblastic leukemia," J Exp Med., 2008, 205(4):751-758.

(56) References Cited

OTHER PUBLICATIONS

Fonesca et al., "Interleukin-6 as a key player in systemic inflammation and joint destruction," Autoimmunity Reviews, 2009, 8(7):538-542.
Fridman et al., "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007 (1 page).
Fridman et al., "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007 (.
Fridman et al., "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov. 8-10, 2007. Poster 0009 (1 page).
Fridman et al., "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA. Nov. 10, 2007. Abstract 1771, poster 285 (1 page).
Fridman et al., "Selective JAK Inhibition is Efficacious against Multiple Myeloma Cells and Reverses the Protective Effects of Cytokine and Stromal Cell Support" Abstract #0956, presented Sunday, Jun. 15, 2008, at the European Hematology Association, 13th Congress, Jun. 12-15, Copenhagen, Denmark (1 page).
Fridman et al., "Preclinical evaluation of local JAK1 and JAK2 inhibition in cutaneous inflammation", Journal of Investigative Dermatology, (Sep. 2011) vol. 131, No. 9, pp. 1838-1844.
Frigault et al., "Abstract #: 0116: A phase 2 study of itacitinib for the prevention of cytokine release syndrome (CRS) induced by immune effector cell (IEC) therapy: preliminary results," Conference Abstract, Presented at the Proceedings of the 48th Annual Meeting of the European Society for Blood and Marrow Transplantation (EBMT), Virtual, Mar. 19-23, 2022; Bone Marrow Transplantation, Nov. 2, 2022, 57(Suppl. 1):72-73.
Fujii et al., "Aberrant expression of serine.thereonine kinase Pim-3 in hepatocellular carcinoma development and its role in the proliferation of human hepatoma cell lines" International Journal of Cancer 114: 209-218, (2005).
Gaestel et al., "Targeting innate immunity protein kinase signalling in inflammation," Nat Rev Drug Discov., Jun. 2009, 8(6):480-99.
Gantner at al., "Concanavalin A-induced T-cell-mediated hepatic injury in mice: the role of tumor necrosis factor," Hepatology, 1995, 21(1):190-198.
Gardner et al., "Decreased Rates of Severe CRS Seen with Early Intervention Strategies for CD19 CAR-T Cell Toxicity Management," ASH 2016, Abstract #586, Dec. 5, 2016, 6 pages.
Gennaro, "Performulation," Remington's Pharmaceutical Sciences, 17th ed., Mack Publishing Company, Easton, Pa., 1985, p. 1418.
Gonzales et al., "Oclacitnib (Apoquel) is a novel Janus Kinase inhibitor with activity against cytokines involved in allergy," Journal of Veterinary Pharmacology and Therapeutics, Aug. 1, 2014, 37(4):317-324.
Goodman, et al., "IL-6 Signaling in Psoriasis Prevents Immune Suppression by Regulatory T Cells," J. Immunol., Sep. 2009, 183: 3170-3176.
Gorre et al., "Clinical Resistance to STI-571 Cancer Therapy Caused by BCR-ABL Gene Mutation or Amplification." Science, 293:876, 2001.
Gottlieb et al., "Psoriasis: Emerging Therapeutic Strategies", Nat Rev Drug Disc., 4:19-34 (2005).
Grabbe et al., "Immunoregulatory mechanisms involved in elicitation of allergic-contact hypersensitivity", Immunol Today, Jan. 19(1):37-44 (1998) (only 1 page provide and marked "best available copy").

Greenberg, "The myelodysplastic syndromes" in Hoffman, et al., eds. Hematology: Basic Principles and Practice (3rd ed.), Churchill Livingston; 2000:1106-1129.
Greene, Protective Groups in Organic Synthesis, 4th ed., John Wiley & Sons: New Jersey, (2007).
Gregory et al., "Clinical and laboratory features of myelofibrosis and limitations of current therapies", Clinical Advances in Hematology and Oncology, (Sep. 2011) vol. 9, No. 9, pp. 1-3.
Grivennikov et al., "IL-6 and STAT3 are required for survival of intestinal epithelial cells and the development of colitis-associated cancer", Cancer Cell, 15:103-111 (2009).
Groneberg et al., "Animal models of allergic and inflammatory conjunctivitis," Allergy, Nov. 2003, 58(11): 1101-13.
Grossman et al., "Interleukin 6 is expressed in high levels in psoriatic skin and stimulates proliferation of cultured human keratinocytes," Proc. Natl. Acad., Sci. USA, Aug. 1989, 86: 6367-6371.
Guschin et al., "A major role for the protein tyrosine kinase JAK1 in the JAK/STAT signal transduction pathway in response to interleukin-6," Embo J, 1995, 14(7):1421-1429.
Hardwicke, et al., "GSK1070916, a potent Aurora B/C kinase inhibitor with broad antitumor activity in tissue culture cells and human tumor xenograft models", Molecular Cancer Therapeutics 8(7), 1808-1817 (2009).
Harigai et al., "Selectivity of Janus Kinase Inhibitors in Rheumatoid Arthritis and Other Immune-Mediated Inflammatory Diseases: Is Expectation the Root of All Headache?" Drugs, 2020, 80:1183-1201.
Harris et al., "World Health Organization classification of neoplastic diseases of the hematopoietic and lymphoid tissues: report of the Clinical Advisory Committee meeting-Airlie House, Virginia, Nov. 1997," J Clin Oncol, Dec. 1999, 17(12): 3835-3849.
Hay et al., "Kinetics and biomarkers of severe cytokine release syndrome after CD19 chimeric antigen receptor-modified T-cell therapy," Immunobio Immunother., Nov. 23, 2017, 130(21):2295-2306.
Hellwig et al., "Fulminant skin GvHD with a cytokine pattern resemblant of cytokine release syndrome successfully treated with multimodal immunosuppression including tocilizumab," Pediatr Blood Cancer. Nov. 2015, 62(11):2033-2035.
Huang, "Inhibition of STAT3 activity with AG490 decreases the invasion of human pancreatic cancer cells in vitro", Cancer Sci. 97(12):1417-23 (2006).
Huarte et al., "Itacitinib (INCB039110), a JAK1 Inhibitor, Reduces Cytokines Associated with Cytokine Release Syndrome Induced by CAR T-cell Therapy," Clinical Cancer Research, 2020, 26:6299-6309.
Indian Office Action in Indian Application No. 11174/DELNP/2015, dated Nov. 19, 2019, 8 pages.
International Preliminary Report on Patentability in International Application No. PCT/US2014/038388, dated Nov. 17, 2015, 7 pages.
International Preliminary Report on Patentability in International Application No. PCT/US2019/018066, dated Aug. 18, 2020, 8 pages.
International Search Report and Written Opinion in International Application No. PCT/US2014/038388, dated Sep. 1, 2014, 9 pages.
International Search Report and Written Opinion in International Application No. PCT/US2019/018066, dated Apr. 12, 2019, 12 pages.
International Search Report and Written Opinion in International Application No. PCT/US2021/035400, dated Aug. 12, 2021, 14 pages.
International Search Report and Written Opinion in International Application No. PCT/US2021/062419, dated Mar. 16, 2022, 15 pages.
Ishizaki, et al., "Pharmacological Properties of Y-27632, a Specific Inhibitor of Rho-Associated Kinases", Molecular Pharmacology, 2000, 57, 976-983.
Itagaki, et al., "Expedient Synthesis of Potent Cannabinoid Receptor Agonist (-)-CP55,940", Organic Letters, 2005; 7(19); 4181-4183.

(56) References Cited

OTHER PUBLICATIONS

Jädersten et al., "Long-term outcome of treatment of anemia in MDS with erythropoietin and G-CSF," Blood, Aug. 2005, 106(3): 803-11.
James, et al., "A unique clonal JAK2 mutation leading to constitutive signalling causes polycythaemia vera", Nature, 434 (7037): 1144-8 (2005).
Janes et al., "Effective and selective targeting of leukemia cells using a TORC1/2 kinase inhibitor.", Nature Medicine (2010) LNKD-PUBMED:20072130, vol. 16, No. 2, pp. 205-213 XP002673719.
Japanese Office Action in Japanese Application No. 2016-514126, dated Feb. 27, 2018, 5 pages (English Translation).
Japanese Office Action in Japanese Application No. 2018-187613, dated Jan. 7, 2020, 4 pages.
Japanese Office Action in Japanese Application No. 2020-543559, dated Feb. 14, 2023, 8 pages.
Jee et al., "Overview: animal models of osteopenia and osteoporosis", J Musculoskel. Neuron, Interact., 1(3):193-207 (2001).
Juvekar and Ruggeri, "Presentation: Preclinical Efficacy, PD and MoA Studies of Ruxolitinib and Itacitinib in Models of GVHD to Support their Clinical Development," Nov. 29, 2017, 36 pages.
Kaercher, "Ocular symptoms and signs in patients with ectodermal dysplasia symdromes", Grafes Arch Clin Exp Ophthalmol, 2004;495-500.
Kamb, "What's wrong with our cancer models?" Nature Reviews Drug Discovery, 2005, 4:161-165.
Kantarjian et al., "Decitabine improves patient outcomes in myelodysplastic syndromes: results of phase III randomized study," Cancer, Apr. 2006, 106(8): 1794-803.
Kato et al., "Airway Epithelial Cells Produce B Cell-Activating Factor of TNF Family by an IFN--Dependent Mechanism1," J of Immunol., Nov. 15, 2006, 177(10):7164-7172.
Kaushansky, K., "Lineage-Specific Hematopoietic Growth Factors", NEJM 354:2034-45 (2006).
Kawamura, et al. (1994). "Molecular cloning of L-JAK, a Janus family protein-tyrosine kinase expressed in natural killer cells and activated leukocytes.", Proc Natl Acad Sci U S A, 91(14): 6374-8).
Kenderian et al., "Ruxolitinib Prevents Cytokine Release Syndrome after Car T-Cell Therapy Without Impairing the Anti-Tumor Effect in a Xenograft Model," Abstracts, Biol Blood Marrow Transplant, 2017, 23:S18-S391.
Kharas, et al., "ABL Oncogenes and Phosphoinositide 3-Kinase: Mechanism of Activation and Downstream Effectors.", Cancer Res., 65(6):2047-2053, Mar. 15, 2005.
Killedar et al., "Early pathogenic events associated with Sjogren's syndrome (SjS)-like disease of the NOD mouse using microarray analysis," Lab Invest, Deember 2006, 86(12): 1243-1260.
Kiss, "Recent developments on JAK2 inhibitors: A patent review", Expert Opinion on Therapeutic Patents, (Apr. 2010) vol. 20, No. 4, pp. 471-495.
Kola, "Can the pharmaceutical industry reduce attrition rates?" Nature Reviews Drug Discovery, 2004, 3:711-715.
Kortylewski, et al., "Regulation of the IL-23 and IL-12 balance by Stat3 signaling in the tumor microenvironment", Cancer Cell, 15:114-123 (2009).
Kruh et al., "The complete coding sequence of arg defines the Abelson subfamily of cytoplasmic tyrosine kinases.", Proc. Natl. Acad. Sci., 87:5802-5806, Aug. 1990.
Kudlacz, et al. "The JAK-3 inhibitor CP-690550 is a potent anti-inflammatory agent in a murine model of pulmonary eosinophilia", European Journal of Pharmacology 582 (2008) 154-161.
Kumar, "Kinase drug discovery approaches in chronic myeloproliferative disorders", Oncogene, (Jun. 18, 2009) vol. 28, No. 24, pp. 2305-2323.
Kurzrock et al., "Serum Interleukin 6 Levels Are Elevated in Lymphoma Patients and Correlate with Survival in Advanced Hodgkin's Disease and with B Symptoms," Cancer Res., May 1993, 52: 2118-2122.
Kurzrock et al., "A Phase I, Open-Label Study of Siltuximab, an Anti-IL-6 Monoclonal Antibody, in Patients with B-cell Non-Hodgkin Lymphoma, Multiple Myeloma, or Castleman Disease," Clin. Cancer Res., published online May 9, 2013, 39 pages.
Lai et al., "Mechanistic Study on the Inactivation of General Acyl-CoA Dehydrogenase by a Metabolite of Hypoglycin A", J. Am. Chem. Soc. 113: 7388-7397 (1991).
Larson, "Myelodysplasia: when to treat and how," Best Pract Res Clin Haematol, 2006, 19(2): 293-300.
Lee et al., "Current concepts in the diagnosis and management of cytokine release syndrome," Blood, May 29, 2014, 124(2):188-195.
Lemp, "The Definition and Classification of Dry Eye Disease: Report of the Definition and Classification Subcommittee of the International Eye Workshop," The Ocular Surface, 5(2): 75-92.
Léo et al., "Identification of a monoclonal antibody specific for a murine T3 polypeptide, " Proc. Natl. Acad. Sci. USA, 1987, 34:1374-1378.
Levine, et al., "Activating mutation in the tyrosine kinase JAK2 in polycythemia vera, essential thrombocythemia, and myeloid metaplasia with myelofibrosis", Cancer Cell, vol. 7, 2005: 387-397.
Levitzki, "Tyrosine kinases as targets for cancer therapy", Eur. J. Cancer 38(suppl. 5):S11-S18 (2002).
Levy, et al. "INCB018424 A Selective Janus Kinase 1/2 Inhibitor" Presentation at the 50th American Society of Hematology Annual Meeting (ASH), Dec. 8, 2008.
Levy, et al., INCB18424 Discussion presentation at the American Society of Hematology, 49th Annual Meeting and Exposition, Atlanta, GA. Abstract #558, Dec. 10, 2007 (25 pages).
Li, et al., "Pim-3, a proto-oncogene with serine/threonine kinase activity, is aberrantly expressed in human pancreatic cancer and phosphorylates Bad-mediated apoptosis in human pancreatic cell lines" Cancer Research 66(13): 6741-7 (2006).
Liesveld et al., Chapter 88. "Myelodysplastic Syndromes (Clonal Cytopenias and Oligoblastic Myelogenous Leukemia)", in Prchal et al., eds. Williams Hematology. 8th ed., New York: McGraw-Hill; 2010, 30 pages.
Lin et al., "Enantioselective synthesis of Janus kinase inhibitor INCB018424 via an organocatalytic aza-Michael reaction," Organic Letters, 2009, 11(9):1999-2002.
Lin, "Constitutive Activation of JAK3/STAT3 in Colon Carcinoma Tumors and Cell Lines", Am J Pathol. 167(4):969-80 (2005).
List et al., "Efficacy of lenalidomide in myelodysplastic syndromes," N Engl J Med, Feb. 2005, 352(6):549-57.
Liu et al., "Cytokines: From Clinical Significance to Quantification," Adv. Sci., Aug. 2021, 8(15):1-29.
Liu, et al., "Combined Inhibition of Janus Kinase 1/2 for the Treatment of JAK2V617F-Driven Neoplasms: Selective Effects on Mutant Cells and Improvements in Measures of Disease Severity", Clin Cancer Res, 2009, 15(22):6891-6900.
Lübbert et al., "Low-dose decitabine versus best supportive care in elderly patients with intermediate- or high-risk myelodysplastic syndrome (MDS) ineligible for intensive chemotherapy: final results of the randomized phase III study of the European Organisation for Research and Treatment of Cancer Leukemia Group and the German MDS Study Group," J Clin Oncol, May 2011, 29(15): 1987-96.
Lübbert, et al., "Cytogenic responses in high-risk myelodysplastic syndrome following low-dose treatment with the DNA methylation inhibitor 5-aza-2'-deoxycytidine," Br J Haematol, Aug. 2001, 114(2): 349-57.
Lube et al., "Evans Syndrome at Childhood-Onset Systemic Lupus Erythematosus Diagnosis: A Large Multicenter Study," Pediatr Blood Cancer, 2016, 63:1238-1243.
Lucet et al., "The structural basis of Janus kinas 2 inhibition by a potent and specific pan-Janus kinase inhibitor," Blood, 2006, 107(1):176-183.
Macchi, et al., "Mutations of Jak-3 gene in patients with autosomal severe combined immune deficiency (SCID)", Nature 377:65-8 (1995).
Madden et al. Comparative study of two non-invasive tear film stability techniques. Curr Eye Res, 1994; 13(4):263-9.
Madhusudan et al., "Tyrosine kinase inhibitors in cancer therapy," Clin Biochem., 2004, 37(7):618-35.
Mainstone et al., "Tear meniscus measurement in the diagnosis of dry eye", Curr Eye Res, 1996; 15:653-661.

(56) References Cited

OTHER PUBLICATIONS

Mancini et al., "RAD 001 (everolimus) prevents mTOR and Akt late re-activation in response to imatinib in chronic myeloid leukemia.", J. Cellular Biochemistry (2010) LNKD-PUBMED:20014066, XP-002673720, 2010, 109(2):320-328.

Mascarenhas, "Primary analysis of a phase II open-label trial of CB039110, a selective JAK1 inhibitor, in patients with myelofibrosis," Haematologica. 2016, pp. 1-22 and Supplemental Data, pp. 1-7.

Maschalidi et al., "Therapeutic effect of JAK1/2 blockade on the manifestations of hemophagocytic lymphoistiocytosis in mice," Blood, May 24, 2016, 128(1):60-71.

Maude et al., "Managing Cytokine Release Syndrome Associated With Novel T Cell- Engaging Therapies," Cancer J., 2014, 20(2):119-122.

Maxson et al., "Oncogenic CSF3R Mutations in Chronic Neutrophilic Leukemia and Atypical CML," N. Engl. J. Med., 2013, 368(19):1781-1790.

McMillan, "The systemic inflammation-based Glasgow Prognostic Score: a decade of experience in patients with cancer," Cancer Treat Rev, Aug. 2013, 39(5): 534-40.

Mesa et al., "Emerging drugs for the therapy of primary and post essential thrombocythemia, post polycythemia vera myelofibrosis", Expert Opinion on Emerging Drugs England, vol. 14, No. 3 (2009) pp. 471-479.

Mesa, et al. "INCB018424, A Selective JAK 1/2 Inhibitor, Significantly Improves the Compromised Nutritional Status and Frank Cachexia in Patients with Myelofibrosis (MF)" Poster #1760 at the American Society of Hematology Annual Meeting (ASH), Dec. 6, 2008 (19 pages).

Mesa, et al., "Evaluating the serial use of the myelofibrosis symptom assessment form for measuring symptomatic improvement: Performance in 87 myelofibrosis patients on a JAK1 and JAK2 inhibitor (INCB018424) clinical trial", Cancer, Nov. 2011, 117(21): 4869-4877.

Mexican Office Action in Mexican Application No. MX/a/2015/015738, dated Aug. 6, 2019, 5 pages.

Meydan et al., "Inhibition of acute lymphoblastic leukaemia by a Jak-2 inhibitor", Nature. Feb. 15, 1996;379(6566):645-8.

Meyer et al., "Anti-inflammatory activity and neutrophil reductions mediated by the JAK1/JAK3 inhibitor, CP-690,550, in rat adjuvant-induced arthritis," Journal of Inflammation, Jan. 1, 2010, pp. 1-12.

Milici et al., "Cartilage preservation by inhibition of Janus kinase 3 in two rodent models of rheumatoid arthritis", Arthritis Research & Therapy, 2008, 10:R14 (http://arthritis-research.com/content/10/1/R14) (9 pages).

Minegishi, et al., "Human Tyrosine Kinase 2 Deficiency Reveals Its Requisite Roles in Multiple Cytokine Signals Involved in Innate and Acquired Immunity", Immunity 25:745-55 (2006).

Mishchenko et al., "Treatment options for hydroxyurea-refractory disease complications in myeloproliferative neoplasms: JAK2 inhibitors, radiotherapy, splenectomy and transjugular intrahepatic portosystemic shunt", Eur J Haematol. Sep. 2010;85(3):192-9. Epub Jun. 2, 2010.

Miyoshi et al., "Interleukin-8 concentrations in conjunctival epithelium brush cytology samples correlate with neutrophil, eosinophil infiltration, and corneal damage", Cornea, 2001;20:743-7.

Molldrem, et al., "Antithymocyte globulin for patients with myelodysplastic syndrome," Br J Haematol, Dec. 1997, 99(3): 699-705.

Moreland, et al. "A Randomized Placebo-Controlled Study of INCB018424, a Selective Janus Kinase 1&2 (JAK 1&2) Inhibitor in Rheumatoid Arthritis (RA)" Presentation at the American College of Rheumatology meeting, Oct. 26, 2008. (20 pages).

Mullighan, "JAK mutations in high-risk childhood acute lymphoblastic leukemia," Proc Natl Acad Sci USA, 2009, 106(23):9414-9418.

Mundle et al., "Evidence for Involvement of Tumor Necrosis Factor-a in Apoptotic Death of Bone Marrow Cells in Myelodysplastic Syndromes, "Am J Hematol, 1999, 60:36-47.

Naka, "The paradigm of IL-6: from basic science to medicine", Arthritis Res., 2002, 4 Suppl 3:S233-42.

Nakagawara, "Trk receptor tyrosine kinases: A bridge between cancer and neural development." Cancer Letters, 169:107-114, 2001.

Naqvi, et al., "A potential role of ruxolitinib in leukemia", Expert Opinion on Investigational Drugs, (Aug. 2011) vol. 20, No. 8, pp. 1159-1166.

National Cancer Institute, "FDA Approval for Ruxolitinib Phosphate", http://www.cancer.gov/cancertopics/druginfo/fda-ruxolitinibphosphate posted Nov. 18, 2011 (3 pages).

Neelapu et al., "Chimeric antigen receptor T-cell therapy—assessment and management of toxicities," Nat Rev Clin Oncol., 2018, 15(1):47-62.

Neidle, Cancer Drug Design and Discovery, Elsevier/Academic Press, 2008, pp. 427-431.

Neubauer, H., et al., "Jak2 Deficiency Defines an Essential Developmental Checkpoint in Definitive Hematopoiesis", Cell, 1998, 93(3):397-409.

Neuner, et al., "Increased IL-6 Production by Monocytes and Keratinocytes in Patients with Psoriasis," J. Invest. Dermatol, 1991, 97:27-33.

Nicholoff et al., "Recent Insights into the immunopathogenesis of psoriasis provide new therapeutic opportunities", J. Clin. Invest., 113; 1664-1675 (2004).

Nishimoto et al., "Improvement in Castleman's disease by humanized anti-interleukin-6 receptor antibody therapy," Blood, 2000, 95(1):56-61.

Norman, "Selective JAK1 inhibitor and selective Tyk2 inhibitor patents," Expert Opinion, Informa Healthcare. 2012, available at: <http://informahealthcare.com/doi/pdfplus/10.1517/13543776.2012.723693>.

Office Action in Chinese Appln. No. 201980024450.5, dated Jan. 18, 2023, 13 pages (with Machine Translation).

Ortmann, et al., "Janus kinases and signal transducers and activators of transcription: their roles in cytokine signaling, development and immunoregulation." Arthritis Res, 2(1): 16-32 (2000).

Ostojic et al., "Ruxolitinib for the treatment of myelofibrosis", Drugs of Today, (Nov. 2011) vol. 47, No. 11, pp. 817-827.

Panteli et al., "Serum interleukin (IL)-1, IL-2, sIL-2Ra, IL-6 and thrombopoietin levels in patients with chronic myeloproliferative diseases, " British Journal of Haematology, 2005, 130, 709-715.

Pardanani, "JAK2 inhibitor therapy in myeloproliferative disorders: rationale, preclinical studies and ongoing clinical trialsJAK2 inhibitor therapy in MPD", Leukemia 22, 23-30 (Jan. 2008).

Parganas et al., "Jak2 is Essential for Signaling through a Variety of Cytokine Receptors", 1998, Cell, 93(3): 385-95.

Park et al., "CP-690550, a Janus Kinase Inhibitor, Suppresses CD4 T-Cell-Mediated Acute Graft-Versus-Host Disease by Inhibiting the Interferon-y Pathway," Transplantation, 2010, 90(8):825-835.

Park et al., "Homogeneous proximity tyrosine kinase assays: scintillation proximity assay versus homogeneous time-resolved fluorescence," Analytical Biochemistry, 1999, 269(1):94-104.

Parks, "Tofacitinib and Other Kinase Inhibitors Offer New Approach to Treating Rheumatoid Arthritis," Rheumatologist, Jun. 2013, pp. 1-12 Available from: <http://www.the-rheumatologist.org/details/article/4871781/Tofacitinib_and_Other_Kinase_Inhibitors_Offer_New_Approach_to_Treating_Rheumatoi.html>, 12 pages.

Pedranzini et al., "Pyridone 6, a pan-Janus-activated kinase inhibitor, induces growth inhibition of multiple myeloma cells," Cancer Res., 2006, 66(19):9714-9721.

Pernis, et al., "JAK-STAT signaling in asthma." J Clin Invest, 109(10): 1279-83 (2002).

Persaud et al., "Plasma pharmacokinetics and distribution of ruxolitinib into skin following oral and topical administration in minipigs," Int J Pharm., Nov. 30, 2020, 590:119889.

Peruvian Office Action in Peruvian Application No. 2406-2015, dated Sep. 26, 2019, 17 pages.

Petri et al., "Baricitinib for systemic lupus erythematosus: a doubleblind, randomised, placebo-controlled, phase 3 trial (SLE-BRAVE-II), " Lancet, 2023, 401:1011-19.

Punwani et al. "Efficacy and safety of topical INCB018424, a selective Janus kinase 1 & 2 (JAK1&2) inhibitor in psoriasis."

(56) References Cited

OTHER PUBLICATIONS

Journal of the American Academy of Dermatology, 350 Park Avenue South, New York, NY 10010-1710, Mosby-Elsevier, 2009, 60(3):1-20.
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008 (15 pages).
Quintas-Cardama et al., "Preclinical characterization of the selective JAK1/2 inhibitor INCB018424: therapeutic implications for the treatment of myeloproliferative neoplasms", Blood First Edition Paper, prepublished online Feb. 3, 2010, American Society of Hematology; DOI 10.1182/blood-2009-04-214957, 115(15):3109-3117.
Raman et al., "Chemokines in health and disease," Exp Cell Res., Mar. 10, 2011, 317(5):575-589.
Rashighi et al., "CXCL10 is critical for the progression and maintenance of depigmentation in a mouse model of vitiligo," Sci Ttansl Med. Feb. 2014, 6(223):233ra23.
Raza et al., "Novel insights into the biology of myelodysplastic syndromes: excessive apoptosis and the role of cytokines," Int J Hematol, Jun. 1996, 63(4): 265-78.
Raza et al., "The myelodysplastic syndromes in 1996: complex stem cell disorders confounded by dual actions of cytokines," Leuk Res, Nov.-Dec. 1996, 20(11-12): 881-90.
Raza et al., "Apoptosis in bone marrow biopsy samples involving stromal and hematopoietic cells in 50 patients with myelodysplastic syndromes," Blood, Jul. 1995, 86(1): 268-76.
Raza et al., "Phase 2 Study of lenalidomide in transfusion-dependent, low-risk, and intermediate-1 risk myelodysplastic syndromes with karyotypes other than deletion 5g," Blood, Jan. 2008, 111(1): 86-93.
Remington's Pharmaceutical Sciences, 17th ed., Mack Publishing Company, Easton, Pa., 1985, p. 1418.
Roberts et al., "Trends in the risks and benefits to patients with cancer participating in phase 1 clinical trials," JAMA, Nov. 2004, 292(17): 2130-40.
Roche, "Bioreversible Carriers in Drug Design," American Pharmaceutical Association and Pergamon Press, 1987, Front Matter Only, 4 pages.
Rodig, et al., "Disruption of the Jak1 gene demonstrates obligatory and nonredundant roles of the Jaks in cytokine-induced biologic responses." Cell, 93(3): 373-83 (1998).
Rothstein et al. "Treatment of vitiligo with the topical Janus kinase inhibitor ruxolitinib," J Am Acad Dermatol., Apr. 7, 2017, 1-8.
Roudebush et al., "Pharmacologic manipulation of a four day murine delayed type hypersensitivity model, " Agents Actions, Jan. 1993, 38(1-2): 116-21.
Rousvoal et al., "Janus kinase 3 inhibition with CP-690,550 prevents allograft vasculopathy", Transpl Int., 2006 19(12): 1014-21.
Samaka et al. "Role of Janus kinase 1 and signal transducer and activator of transcription 3 in vitiligo," Clin Cosmet Investig Dermatol., 2019, 12:469-480.
Samanta et al., "Janus kinase 2: a critical target in chronic myelogenous leukemia", Cancer Res. Jul. 1, 2006;66(13):6468-72.
Schiffer, "Clinical issues in the management of patients with myelodysplasia," Hematology Am Soc Hematol Educ Program, 2006: 205-10.
Schiffer, "Myelodysplasia: the good, the fair and the ugly," Best Pract Res Clin Haematol, Mar. 2007, 20(1): 49-55.
Schindler et al., "Hormones and Signaling: Cytokines and STAT Signaling", Adv Pharmacol. 2000; 47:113-74.
Schrader et al., "Animal models of dry eye," Dev Opthalmol, 2008, 41:298-312.
Schram et al., "How I treat hemophagocytic lymphohistiocytosis in the adult patient," Blood, 2005, 125(19):2908-2914.
Schroeder et al., "A Phase I Trial of Janus Kinase (JAK) Inhibition with INCB039110 in Acute Graft-Versus-Host Disease (aGVHD)," Blood, Dec. 3-6, 2016, 128(22) 3 pages.
Science IP Search Report, Mar. 2021, 421 pages.
Scott, et al., "Jaks, STATs, Cytokines, and Sepsis." Clin Diagn Lab Immunol, 9(6):1153-9 (2002).
Search Report Id SR-20210895.01, "Single Crystal Structure Determination of INCB054707 Phosphate," dated May 20, 2021, 42 pages.
Seki, "STAT3 and MAPK in human lung cancer tissues and suppression of oncogenic growth by JAB and dominant negative STAT3", Int J Oncol. 24(4):931-4 (2004).
Seto, et al. (2003). "Enhanced Th2 cell-mediated allergic inflammation in Tyk2- deficient mice." J Immunol, 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia." Cancer Cell, 2:117-125, Aug. 2002.
Shi, et al., "The pharmacokinetics, pharmacodynamics, and safety of orally dosed INCB018424 phosphate in healthy volunteers", Journal of Clinical Pharmacology, (Dec. 2011) vol. 51, No. 12, pp. 1644-1654.
Shimizu et al., "Distinct cytokine profile in juvenile systemic lupus erythematosus-associated macrophage activation syndrome," Clin Immunol., Feb. 2013, 146(2):73-76.
Silverman et al., "Further analysis of trials with azacitidine in patients with myelodysplastic syndrome: studies 8421, 8921, and 9221 by the Cancer and Leukemia Group B," J Clin Oncol, Aug. 2006, 24(24): 3895-903.
Silverman et al., "Randomized controlled trial of azacitidine in patients with the myelodysplastic syndrome: a study of the cancer and leukemia group B," J Clin Oncol, May 2002, 20(10): 2429-40.
Singh, et al., "Serum concentration of IL-6, IL-2, TNF-$\alpha$, and IFN$\gamma$ in Vitiligo patients," Indian J Dermatology., Jan.-Feb. 2012, 57(1):12-14.
Sloand et al., "Factors affecting response and survival in patients with myelodysplasia treated with immunosuppressive therapy," J Clin Oncol, May 2008, 26(15): 2505-11.
Smith et al., "Basic pathogenic mechanisms operating in experimental models of acute anterior uveitis," Immunol Cell Biol, Dec. 1998, 76(6): 497-512.
Smolen et al., "Effect of interleukin-6 receptor inhibition with tocilizumab in patients with rheumatoid arthritis (OPTION study): a double-blind, placebo-controlled, randomised trial," Lancet, 2008, 371:987-997.
Smolen, et al., "Effect of interleukin-6 receptor inhibition with tocilizumab in patients with rheumatoid arthritis (OPTION study): a double-blind, placebo-controlled, randomized trial", Lancet 371:987, 2008 (2008).
Snodgrass et al., "Cytokine Release Syndrome: CD19-directed CAR T cell therapy, Bispecifics & Haploidentical HSCT," Nov. 22, 2017, 33 pages.
Sonbol et al., "Comprehensive review of JAK inhibitors in myeloproliferative neoplasms," Therapeutic Advances in Hematology, 2013, 4(1): 15-35.
Song et al. "JAK1 Activates STAT3 Activity in Non-Small-Cell Lung Cancer cells and IL-6 Neutralizing Antibodies can Suppress JAK1-STAT3 Signaling," Mol Cancer Ther., Mar. 2011, 10(3): 481-94.
Spoerl et al., "Activity of therapeutic JAK 1/2 blockade in graft-versus-host disease," Blood, Jun. 2014, 123(24): 3832-42.
Sriram et al., "Induction of gp130-related Cytokines and Activation of JAK2/STAT3 Pathway in Astrocytes Precedes Up-regulation of Glial Fibrillary Acidic Protein in the 1-Methyl-4-phenyl-1,2,3,6-tetrahydropyridine Model of Neurodengeneration", J. Biol Chem, May 2004, 279(19):19936-47.
Staerk, J., et al., "JAK1 and Tyk2 activation by the homologous polycythemia vera JAK2 V617F mutation: cross-talk with IGF1 receptor", J Biol Chem., 280:41893-41899 (2005).
Stirewalt et al., "Predictors of relapse and overall survival in Philadelphia chromosome-positive acute lymphoblastic leukemia after transplantation", Biol Blood Marrow Transplant. Mar. 2003;9(3):206-12.

(56) References Cited

OTHER PUBLICATIONS

Strassmann et al., "Suramin Interferes with Interleukin-6 Receptor Binding in Vitro and Inhibits Colon-26-mediated Experimental Cancer Cachexia in Vivo," J. Clin. Invest., Nov. 1993, 92: 2152-2159.
Symington et al., "The relationship of serum IL-6 levels to acute graft-versus-host disease and hepatorenal disease after human bone marrow transplantation," Transplantation, Sep. 1992, 54(3): 457-62.
Taiwanese Office Action in Taiwanese Application No. 112110278, dated Aug. 16, 2023, 11 pages (with English Translation).
Taiwanese Office Action in Taiwanese Application No. 112110278, dated Nov. 28, 2023, 8 pages (with English Translation).
Takemoto, et al. (1997). "Proliferation of adult T cell leukemia/lymphoma cells is associated with the constitutive activation of JAK/STAT proteins." Proc Natl Acad Sci USA, 94(25): 13897-902.
Tamura et al., "Involvement of Human Interleukin 6 in Experimental Cachexia Induced by a Human Uterine Cervical Carcinoma Xenograft," Clin. Cancer Res., Nov. 1995, 1: 1353-1358.
Taylor et al., "The JAK1-Selective Inhibitor Filgotinib Displays an Anti- Inflammatory Biomarker Signature in Rheumatoid Arthritis Patients," 2016 ACR/ARHP Annual Meeting, Abstract No. 2616, Sep. 28, 2016.
Teachey et al., "Identification of Predictive Biomarkers for Cytokine Release Syndrome after Chimeric Antigen Receptor T cell Therapy for Acute Lymphoblastic Leukemia," Cancer Discov. 6, 664-679 (2016).
Tefferi et al., "The Clinical Phenotype of Myelofibrosis Encompasses a Chronic Inflammatory State that is Favorably Altered by INCB018424, A Selective Inhibitor of JAK1/2" Poster #2804 at the American Society of Hematology Annual Meeting (ASH), Dec. 7, 2008, (18 pages).
Tefferi, "Primary myelofibrosis: 2012 update on diagnosis, risk stratification, and management", American Journal of Hematology, (Dec. 2011) vol. 86, No. 12, pp. 1017-1026.
Tefferi, et al., "Serious adverse events during ruxolitinib treatment discontinuation in patients with myelofibrosis", Mayo Clinic Proceedings, (Dec. 2011) vol. 86, No. 12, pp. 1188-1191.
Tisoncik et al., "Into the Eye of the Cytokine Storm," Microbiology and Molecular Biology Reviews, Mar. 2012, 76(1):16-32.
Toyonaga, "Blockade of constitutively activated Janus kinase/signal transducer and activator of transcription-3 pathway inhibits growth of human pancreatic cancer", Cancer Lett. 201(1):107-16 (2003).
Traves et al., "JAK selectivity and the implications for clinical inhibition of pharmacodynamic cytokine signalling by filgotinib, upadacitinib, tofacitinib and baricitinib," Ann Rheum Dis, 2021, 80:865-875.
Trikha et al., "Targeted anti-interleukin-6 monoclonal antibody therapy for cancer: a review of the rationale and clinical evidence," Clinical Cancer Research, 2003, 9: 4653-4665.
Vanhoutte, "Selective JAK1 Inhibition in the Treatment of Rheumatoid Arthritis: Proof of Concept with GLPG0634, "Arthritis Rheum 64.10 (2012): S1051-1.
Vannucchi et al., "Inhibitors of PI3K/Akt and/or mTOR Inhibit the Growth of Cells of Myeloproliferative Neoplasms and Synergize with JAK2 Inhibitor and Interferon", Blood, vol. 118, No. 21, pp. 1638-1639, XP008150742 ASH Annual Meeting Abstract 3835 American Society of Hematology.
Vannucchi et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)", Blood, ASH Annual Meeting Abstracts 307, 2009, 114(22), 2 pages.
Vannucchi et al., "The mTOR Inhibitor, RAD001, Inhibits the Growth of Cells From Patients with Myeloproliferative Neoplasms", Blood: ASH Annual Meeting Absracts, 51$^{st}$ Annual Meeting of the American Society of Hematology, 2009, 114(22) , 2 page.
Vardiman et al., "The 2008 revision of the World Health Organization (WHO) classification of myeloid neoplasms and acute leukemia: rationale and important changes," Blood, Jul. 2009, 114(5): 937-51.
Vardiman et al., "The World Health Organization (WHO) classification of the myeloid neoplasms," Blood, Oct. 2002, 100(7): 2292-302.
Verma, et al., "Jak family of kinases in cancer", Cancer and Metastasis Reviews, vol. 22, No. 4, 423-434, DOI: 10.1023/A:1023805715476 (2003).
Verstovsek et al., "Characterization of JAKS V617F Allele Burden in Advanced Myelofibrosis (MF) Patients: No Change in V617F:WT JAK2 Ratio in Patients with High Allele Burdens despite Profound Clinical Improvement Following Treatment with the JAKL Inhibitor, INCB018424," 50th ASH Annual Meeting and Exposition, Abstract No. 2802 (2008).
Verstovsek et al., "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008, at the European Hematology Association, 13th Congress, June 12-15, Copenhagen, Denmark (2 pages).
Verstovsek et al., INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007 (16 pages).
Verstovsek, "Therapeutic Potential of JAK2 Inhibitors", Hematology Am Soc Hematol Educ Program, 2009:636-42.
Verstovsek, et al., Blood (ASH Annual Meeting Abstracts) 2007 110: Abstract 558.
Verstovsek, et al., Blood (ASH Annual Meeting Abstracts) 2009 114: Abstract 311.
Verstovsek, et al., Blood (ASH Annual Meeting Abstracts) 2010 116: Abstract 313.
Verstovsek, S. et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008 (19 pages).
Vietnamese Office Action in Vietnamese Application No. 11-2019-01578, dated Apr. 26, 2019, 2 pages.
Vietnamese Office Action in Vietnamese Application No. 1-2020-05311, dated Jul. 26, 2023, 4 pages (with English Translation).
Wagh et al., "Polymers used in ocular dosage form and drug delivery systems," Asian J. Pharma, 12-17.
Williams et al., "Initial Efficacy of INCB018424, a selective Janus Kinase1& 2 (JAK1&2) Inhibitor in Rheumatoid Arthritis (RA)," European League Against Rheumatism (EULAR) meeting presentation and abstract (Jun. 11-14, 2008, Paris, France). Annals Rheum Dis 67SII:62, 2008.
www.quora.com, "What is a 'cytokine storm,' and what are the diseases that cause that?", retrieved on Feb. 18, 2018, retrieved from URL <https://www.quora.com/What-is-a-cytokine-storm-and-what-are-the-diseases-that-cause-that>, 9 pages.
Xiaoyang et al., "Knockdown of STAT3 Expression by RNA Interference Inhibits the Induction of Breast Tumors in Immunocompetent Mice", Cancer Res, Apr. 1, 2005, 65:2532.
Xiong, "Inhibition of JAK1, 2/STAT3 Signaling Induces Apoptosis, Cell Cycle Arrest, and Reduces Tumor Cell Invasion in Colorectal Cancer Cells," Neoplasia, Mar. 2008, 10(3): 287-297.
Xu et al., "Cytokine release syndrome in cancer Immunotherapy with chimeric antigen receptor engineered T cells," Cancer Lett., 2014, 343(2):172-178.
Yamamura et al., "Circulating interleukin-6 levels are elevated in adult T-cell leukaemia/lymphoma patients and correlate with adverse clinical features and survival, " Br. J. Haematol., 1998, 100: 129-134.
Yamaoka et al., "Janus kinase (JAK) inhibitors in rheumatoid arthritis", Current Rheumatology Reviews, (Nov. 2011) vol. 7, No. 4, pp. 306-312.
Yang et al., "Constitutive NF-KB activation confers interleukin 6 (IL6) independence and resistance to dexamethasone and Janus

(56) References Cited

OTHER PUBLICATIONS kinase inhibitor INCB018424 in murine plasmacytoma cells", Journal of Biological Chemistry, Aug. 2011, 286(32):27988-27997.
Yao, et al. "Glucocorticoid-Induced Bone Loss in Mice Can Be Reversed by the Actions of Parathyroid Hormone and Risedronate on Different Pathways for Bone Formation and Mineralization", Arthritis and Rheumatism, 58(11):3485-3497 (2008).
Yao, et al., "Glucocorticoid Excess in Mice Results in Early Activation of Osteoclastogenesis and Adipogenesis and Prolonged Suppression of Osteogenesis", Arthritis and Rheumatism, 58(6), 1674-1686 (2008).
Yongjun et al., "Advances in research of tyrosine kinases inhibitor of vascular endothelial growth factor receptor," Chinese J New Drugs, Dec. 31, 2008, 17(7):544-550.
Younes et al., "Phase I Study of a Novel Oral Janus Kinase 2 Inhibitor, SB1518, in Patients With Relapsed Lymphoma: Evidence of Clinical and Biologic Activity in Multiple Lymphoma Subtypes," Journal of Clinical Oncology, Nov. 2012, 30(33): 4161-4167.
Yu et al., "Constitutive activation of the Janus kinase-STAT pathway in T lymphoma overexpressing the Lck protein tyrosine kinase", J Immunol. 159(11):5206-10 (1997).
Zhang et al., "An analytical biomarker for treatment of patients with recurrent B-ALL after remission induced by infusion of anti-CD19 chimeric antigen receptor T (CAR-T) cells," Sci China Life Sci., Apr. 2016, 59(4):379-385.
Zhang et al., "The efficacy and safety of tofacitinib, peficitinib, solcitinib, baricitinib, abrocitinib and deucravacitinib in plaque psoriasis—A network meta-analysis," JEADV, 2022, 36:1937-1946.
Zheng et al., "Discovery of INCB108201PF-4178903, a potent, selective, and orally bioavailable dual CCR2 and CCR5 antagonist", Bioorganic & Medicinal Chemistry Letters 21 (2011) 1442-45.
Zou et al., "Signaling Pathways Activated by Oncogenic Forms of Abl Tyrosine Kinase." Journal of Biological Chemistry, 1999, 274(26):18141-18144.
Eurasian Office Action in Eurasian Application No. 202390267, dated Sep. 30, 2024, 8 pages (with English Translation).
Israeli Office Action in Israeli Application No. 311485, dated Sep. 11, 2024, 5 pages.
Japanese Office Action in Japanese Application No. 2023-187800, dated Nov. 26, 2024, 7 pages (with Machine Translation).
Korean Office Action in Korean Application No. 10-2020-7026669, dated Aug. 28, 2024, 9 pages (with English Translation).
Korean Office Action in Korean Application No. 10-2024-7035396, dated Dec. 19, 2024, 11 pages (with English Translation).
Korean Office Action in Korean Application No. 10-2024-7035403, dated Dec. 16, 2024, 11 pages (with English Translation).
Philippines Office Action in Philippines Application No. 1-2020-551251, dated Sep. 3, 2024, 6 pages.
Ruscitti et al., "Advances in immunopathogenesis of macrophage activation syndrome during rheumatic inflammatory diseases: toward new therapeutic targets?," Expert Review of Clinical Immunology, 2017, 13(11):1041-1047, 26 pages (Author Manuscript).
Canadian Office Action in Canadian Application No. 3091339, dated Feb. 21, 2025, 6 pages.

JAK1 PATHWAY INHIBITORS FOR THE TREATMENT OF CYTOKINE-RELATED DISORDERS

TECHNICAL FIELD

This disclosure relates to JAK1 pathway inhibitors and the use thereof in treating cytokine-related diseases or disorders.

BACKGROUND

Cytokine-related diseases or disorders are characterized by excessive immune activation and include cytokine release syndrome (CRS), hemophagocytic lymphohistiocytosis (HLH), macrophage activation syndrome (MAS), and CAR-T-cell-related encephalopathy syndrome (CRES).

Cytokine release syndrome (CRS) is a direct result of overproduction of inflammatory cytokines caused by supraphysiological levels of immune activation and is manifested as a clinical constellation of symptoms including fever, nausea, fatigue, myalgia, malaise, hypotension, hypoxia, capillary leak, resulting in potential multi-organ toxicity.

CRS is an unwanted side effect of, e.g., immune-based therapies for serious disease states such as cancer. Immune-based therapies that can result in CRS include administration of monoclonal antibodies (mAbs) and, more recently, adoptive T-cell therapies for cancer. Lee et al. *Blood.* 2014, 124(2): 188-195. For example, chimeric antigen receptor (CAR) T-cell therapy uses altered T-cells to target cancers and is already approved by the FDA for use in certain forms of refractory non-Hodgkin lymphoma and pediatric relapsed lymphoblastic leukemia (ALL).

The cytokine profiles involved in CRS encompass two main cellular sources: T lymphocyte derived cytokines including interferon-gamma (IFN)-γ, IL-2, IL-6, soluble IL-6 receptor (IL-6R) and granulocyte-macrophage colony stimulating factor (GM-CSF); and cytokines mainly secreted by the monocytes and/or macrophages such as IL-1β, IL-6, IL-12, IL-18, and tumor necrosis factor (TNF)-α. Xu X J, Tang Y M. *Cancer Lett.* 2014; 343:172-8. Zhang Y., et al. *Sci China Life Sci.* 2016; 59:379-85. Brentjens R., et al. *Mol Ther.* 2010; 18:666-8.

Modulation of the exaggerated cytokine response resulting in CRS has the potential to provide significant clinical benefit. For example, tocilizumab, an antibody against the IL-6 receptor (IL-6R), decreases the rates of severe CRS and is FDA approved for use in CRS. However, tocilizumab's mechanism of action is restricted to anti-IL-6R only.

Hemophagocytic lymphohistiocytosis (HLH), another syndrome of excessive or uncontrolled immune activation, occurs mostly in infants from birth to 18 months of age, but can also occur in adults. HLH can be primary (familial) or secondary, meaning it occurs in the setting of other infectious, malignant, rheumatologic, or metabolic conditions. Symptoms of HLH include cytopenias, hepatosphlenomegaly, and fevers. Schram, A. and Berliner, N. *Blood.* 2005. 125(19), 2908-2914.

Macrophage activation syndrome (MAS) is clinically presented in a manner similar to HLH (and even considered a secondary or acquired for of HLH) and is an episode of increased inflammation associated with infection, rheumatic disease, or malignancy. Borgia, R. E. et al. *Arthritis Rheumatol.,* 2018, doi: 10.1002/art.40417, pre-publication. MAS was initially described as associated with juvenile idiopathic arthritis, but is also a increasingly recognized as a complication of other diseases such as childhood-onset systemic lupus erythematosus (cSLE). Shimizu M., et al. *Clin Immunol.* 2013 February; 146(2):73-6. The development of MAS is characterized by a substantial increase in numerous pro-inflammatory cytokines, i.e., a cytokine storm. Borgia, R. E. et al. *Arthritis Rheumatol.,* 2018, doi: 10.1002/art.40417, pre-publication. MAS is a life-threatening condition with high mortality rates: 8-22% in pediatric autoimmune diseases generally and 10-22% in MAS complicating cSLE. Borgia, R. E. et al. *Arthritis Rheumatol.,* 2018, doi: 10.1002/art.40417, pre-publication.

CAR-T-cell related encephalopathy syndrome (CRES) is the second most common adverse event, after CRS, associated with CAR-T-cell therapy. CRES is typically characterized by a toxic encephalopathy state with symptoms of confusion and delirium and occasional seizures and cerebral edema. The manifestation of CRES can be biphasic with symptoms occurring within the first 5 days and/or 3-4 weeks after cellular immunotherapy. The pathophysiological mechanism is believed to involve passive diffusion of cytokines into the brain of patients treated with CAR-T-cell therapy. The reduction or elimination of this mechanism can be beneficial to such patients. Neelapu, et al. *Nat Rev Clin Oncol.* 2018, 15(1) 47-62.

Accordingly, there is a need to develop new therapies for the treatment of cytokine-related diseases or disorders. This application addresses this need and others.

DESCRIPTION OF THE DRAWINGS

FIG. 2A shows the inhibition of IL-6. FIG. 2B shows the inhibition of IFNγ. FIG. 2C shows the inhibition of GM-CSF.

FIG. 3A shows the inhibition of IL-12. FIG. 3B shows the inhibition of IL-1β. FIG. 3C shows the inhibition of IL-18.

SUMMARY

Provided herein are methods for the treatment of a cytokine-related disease or disorder in a subject in need thereof, comprising administering to said patient a therapeutically effective amount of a JAK1 pathway inhibitor, or a pharmaceutically acceptable salt thereof.

Provided herein is a JAK1 pathway inhibitor, or a pharmaceutically acceptable salt thereof, for the treatment of a cytokine-related disease or disorder in a subject in need thereof.

Provided herein is a use of a JAK1 pathway inhibitor, or a pharmaceutically acceptable salt thereof, for manufacture of a medicament for use in treating a cytokine-related disease or disorder in a subject in need thereof.

DETAILED DESCRIPTION

The present invention provides, inter alia, a method of treating a cytokine-related disease or disorder in a subject in need thereof, comprising administering to said subject a therapeutically effective amount of a JAK1 pathway inhibitor, or a pharmaceutically acceptable salt thereof.

The methods described herein utilize JAK1 pathway inhibitors, particularly JAK1 selective inhibitors. A JAK1 selective inhibitor is a compound that inhibits JAK1 activity preferentially over other Janus kinases. JAK1 plays a central role in a number of cytokine and growth factor signaling pathways that, when dysregulated, can result in or contribute to disease states. For example, IL-6 levels are elevated in rheumatoid arthritis, a disease in which it has been suggested to have detrimental effects (Fonesca, et al., *Autoimmunity Reviews*, 8:538-42, 2009). Because IL-6 signals, at least in part, through JAK1, IL-6 can be indirectly through JAK1 inhibition, resulting in potential clinical benefit (Guschin, et al. *Embo J* 14:1421, 1995; Smolen, et al. *Lancet* 371:987, 2008). Moreover, in some cancers JAK1 is mutated resulting in constitutive undesirable tumor cell growth and survival (Mullighan, *Proc Natl Acad Sci USA*. 106:9414-8, 2009; Flex, *J Exp Med*. 205:751-8, 2008). In other autoimmune diseases and cancers, elevated systemic levels of inflammatory cytokines that activate JAK1 may also contribute to the disease and/or associated symptoms. Therefore, patients with such diseases may benefit from JAK1 inhibition. Selective inhibitors of JAK1 may be efficacious while avoiding unnecessary and potentially undesirable effects of inhibiting other JAK kinases.

Figure 4:
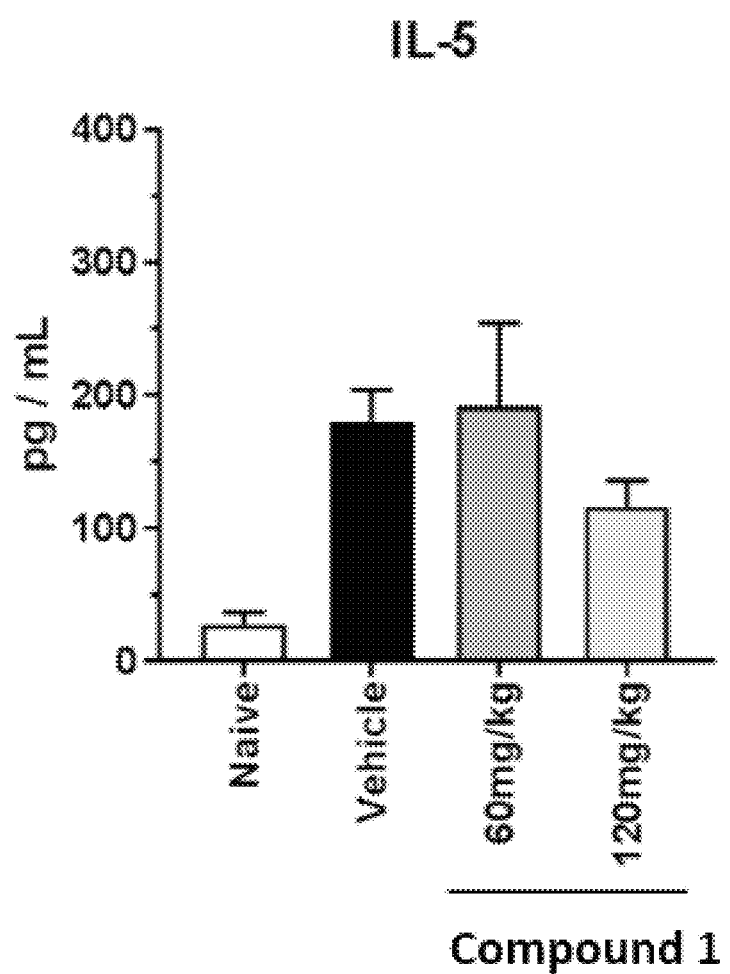
FIG. 4 shows that cytokine IL-5 is unaffected by Compound 1 treatment during concanavalin A induced cytokine release syndrome (see Example C).

A JAK1 pathway inhibitor, specifically Compound 1 (i.e., {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, see Table 1), achieves highly effective dose-dependent modulation of CRS-relevant inflammatory cytokines (see, e.g., Examples B and C, and FIGS. 1, 2A-2C, and 3A-3C). Surprisingly, the therapeutic profile encompasses multiple pathogenic cytokines and is not restricted to IL-6/IL-6R axis only (unlike, e.g., tocilizumab). Efficacy is achieved by inhibiting cytokines derived from T-cells and monocyte / macrophages with high clinical relevance to CRS pathogenesis. Further, the data presented herein in connection with JAK1 inhibitor Compound 1 shows that treatment benefit is achieved without broad cytokine immunosuppression (as demonstrated by unchanged IL-5 levels) (FIG. 4).

In some embodiments, the cytokine-related disease or disorder is cytokine release syndrome (CRS), hemophagocytic lymphohistiocytosis (HLH), macrophage activation syndrome (MAS), or CAR-T-cell-related encephalopathy syndrome (CRES).

In some embodiments, the cytokine-related disease or disorder is cytokine release syndrome (CRS).

In some embodiments, the cytokine-related disease or disorder is hemophagocytic lymphohistiocytosis (HLH).

In some embodiments, the cytokine-related disease or disorder is macrophage activation syndrome (MAS). In some embodiments, the macrophage activation syndrome is associated with systemic juvenile idiopathic arthritis. In some embodiments, the macrophage activation syndrome is associated with pediatric systemic lupus erythematosus.

In some embodiments, the cytokine-related disease or disorder is CAR-T-cell-related encephalopathy syndrome (CRES).

In some embodiments, the present application provides a method of treating cytokine release syndrome in a subject, comprising administering a CAR-T cell therapy to said subject and a JAK1 pathway inhibitor, or a pharmaceutically acceptable salt thereof. In some embodiments, treating is ameliorating or inhibiting. In some embodiments, treating is preventing.

In some embodiments, the JAK1 pathway inhibitor, or a pharmaceutically acceptable salt thereof, is administered simultaneously with the CAR-T cell therapy.

In some embodiments, the JAK1 pathway inhibitor, or a pharmaceutically acceptable salt thereof, is administered after the administration of the CAR-T cell therapy.

In some embodiments, the CAR-T cell therapy is axicabtagene ciloleucel.

In some embodiments, the CAR-T cell therapy is tisagenlecleucel.

In some embodiments, the subject suffers from a B-cell malignancy.

In some embodiments, the subject suffers from diffuse large B-cell lymphoma (DLBCL), primary mediastinal large B-cell lymphoma, high-grade B-cell lymphoma, transformed follicular lymphoma, or acute lymphoblastic leukemia.

In some embodiments, the JAK1 pathway inhibitor, or a pharmaceutically acceptable salt thereof, is selective for JAK1 over JAK2, JAK3, and TYK2 (i.e., a JAK1 selective inhibitor). For example, the compounds described herein, or pharmaceutically acceptable salts thereof, preferentially inhibit JAK1 over one or more of JAK2, JAK3, and TYK2. In some embodiments, the compounds inhibit JAK1 preferentially over JAK2 (e.g., have a JAK2/JAK1 $IC_{50}$ ratio >1).

In some embodiments, the compounds or salts are about 10-fold more selective for JAK1 over JAK2. In some embodiments, the compounds or salts are about 3-fold, about 5-fold, about 10-fold, about 15-fold, or about 20-fold more selective for JAK1 over JAK2 as calculated by measuring $IC_{50}$ at 1 mM ATP (e.g., see Example A).

In some embodiments, the JAK1 pathway inhibitor is a compound of Table 1, or a pharmaceutically acceptable salt thereof. The compounds in Table 1 are selective JAK1 inhibitors (selective over JAK2, JAK3, and TYK2). The $IC_{50}$ values obtained by the method of Example A at 1 mM ATP are shown in Table 1.

TABLE 1

| Comp. No. | Prep. | Name | Structure | JAK1 IC$_{50}$ (nM) | JAK2/ JAK1 |
|---|---|---|---|---|---|
| 1 | US 2011/ 0224190 (Example 1) | {1-{1-[3-Fluoro-2-(trifluoromethyl)isonico-tinoyl]piperidin-4-yl}-3-[4-(7H-pyrrolo[2,3-d]pyrimidin-4-yl)-1H-pyrazol-1-yl]azetidin-3-yl}acetonitrile | 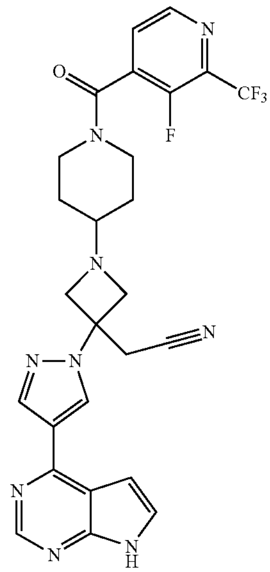 [SMILES: N#CCC1(n2cc(-c3ncnc4[nH]ccc34)cn2)CN(C2CCN(C(=O)c3ccnc(C(F)(F)F)c3F)CC2)C1] | + | >10 |
| 2 | US 2011/ 0224190 (Example 154) | 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide | 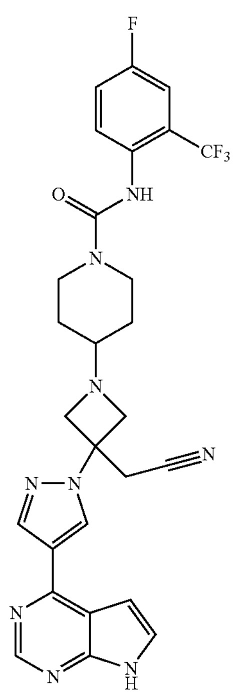 [SMILES: N#CCC1(n2cc(-c3ncnc4[nH]ccc34)cn2)CN(C2CCN(C(=O)Nc3ccc(F)cc3C(F)(F)F)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 3 | US 2011/ 0224190 (Example 85) | [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile | 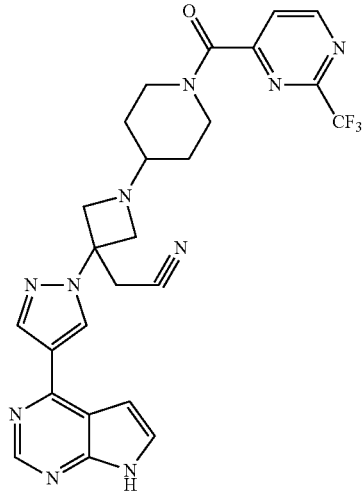 [SMILES: N#CCC1(n2cc(-c3ncnc4[nH]ccc34)cn2)CN(C2CCN(C(=O)c3ccnc(C(F)(F)F)n3)CC2)C1] | + | >10 |
| 4 | US 2014/ 0343030 (Example 7) | 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide | 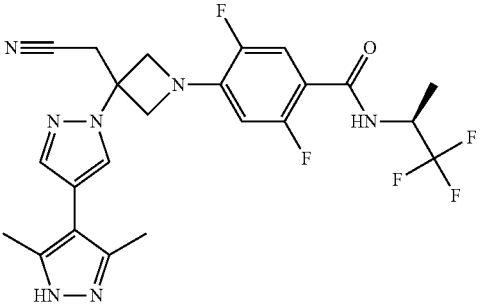 [SMILES: Cc1n[nH]c(C)c1-c1cnn(C2(CC#N)CN(c3cc(F)c(C(=O)N[C@@H](C)C(F)(F)F)cc3F)C2)c1] | +++ | >10 |
| 5 | US 2014/ 0121198 (Example 20) | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 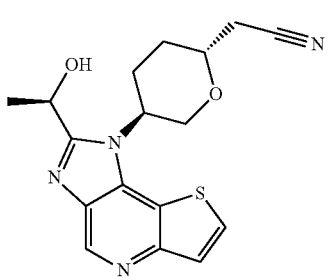 [SMILES: C[C@@H](O)c1nc2cnc3ccsc3c2n1[C@H]1CC[C@H](CC#N)OC1] | ++ | >10 |
| 6 | US 2010/ 0298334 (Example 2)$^a$ | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile | 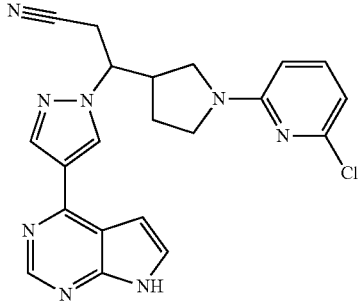 [SMILES: N#CCC(C1CCN(c2cccc(Cl)n2)C1)n1cc(-c2ncnc3[nH]ccc23)cn1] | + | >10 |

TABLE 1-continued

| Comp. No. | Prep. | Name | Structure | JAK1 IC$_{50}$ (nM) | JAK2/JAK1 |
|---|---|---|---|---|---|
| 7 | US 2010/0298334 (Example 13c) | 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile | 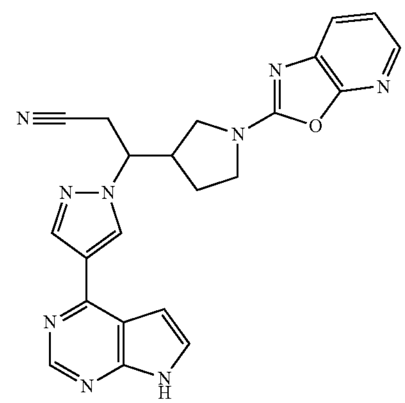 [SMILES: N#CCC(C1CCN(c2nc3cccnc3o2)C1)n1cc(-c2ncnc3[nH]ccc23)cn1] | + | >10 |
| 8 | US 2011/0059951 (Example 12) | 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile | 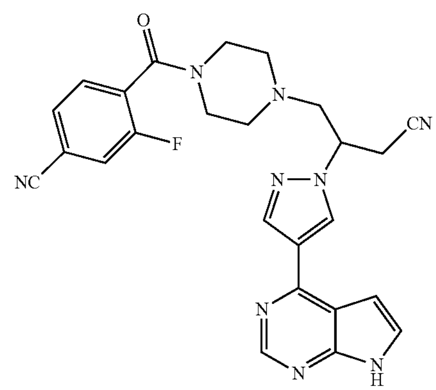 [SMILES: N#CCC(CN1CCN(C(=O)c2ccc(C#N)cc2F)CC1)n1cc(-c2ncnc3[nH]ccc23)cn1] | + | >10 |
| 9 | US 2011/0059951 (Example 13) | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 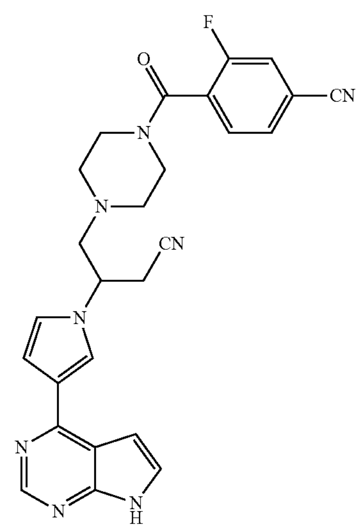 [SMILES: N#CCC(CN1CCN(C(=O)c2ccc(C#N)cc2F)CC1)n1ccc(-c2ncnc3[nH]ccc23)c1] | + | >10 |

TABLE 1-continued

| Comp. No. | Prep. | Name | Structure | JAK1 IC$_{50}$ (nM) | JAK2/ JAK1 |
|---|---|---|---|---|---|
| 10 | US 2012/ 0149681 (Example 7b) | [trans-1-[4-(7H-pyrrolo[2,3-d]pyrimidin-4-yl)-1H-pyrazol-1-yl]-3-(4-{[2-(trifluoromethyl) pyrimidin-4-yl]carbonyl}piperazin-1-yl)cyclobutyl]acetonitrile | 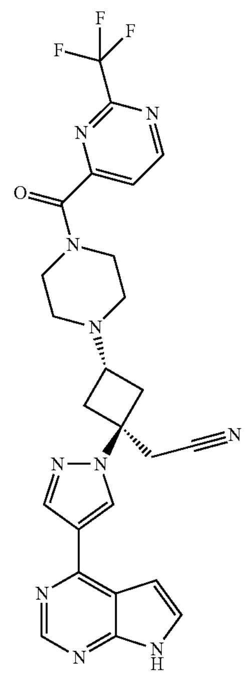 [SMILES: N#CC[C@]1(n2cc(-c3ncnc4[nH]ccc34)cn2)C[C@H](N2CCN(C(=O)c3ccnc(C(F)(F)F)n3)CC2)C1] | + | >10 |
| 11 | US 2012/ 0149681 (Example 157) | {trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 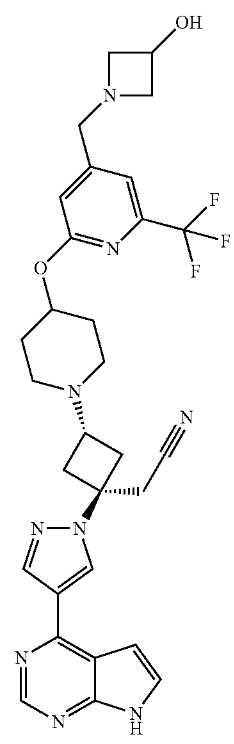 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] | + | >10 |

TABLE 1-continued

| Comp. No. | Prep. | Name | Structure | JAK1 IC$_{50}$ (nM) | JAK2/JAK1 |
|---|---|---|---|---|---|
| 12 | US 2012/0149681 (Example 161) | {trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 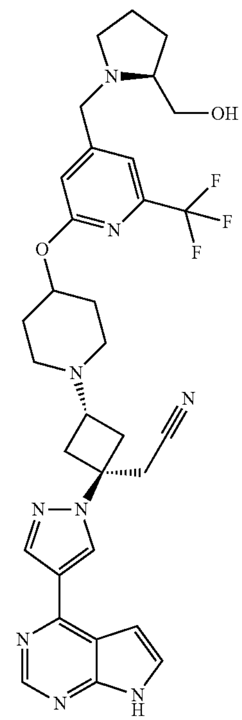 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] | + | >10 |
| 13 | US 2012/0149681 (Example 162) | {trans-3-(4-{[4-{[(2R)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 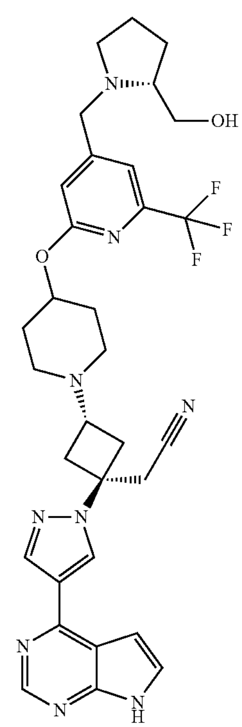 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 14 | US 2012/ 0149682 (Example 20)[b] | 4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile | 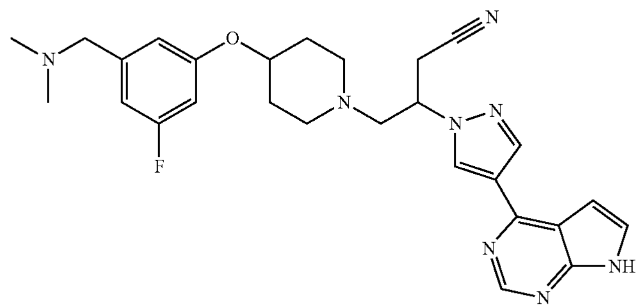 [SMILES: CN(C)Cc1cc(F)cc(OC2CCN(CC(CC#N)n3cc(-c4ncnc5[nH]ccc45)cn3)CC2)c1] | + | >10 |
| 15 | US 2013/ 0018034 (Example 18) | 5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide | 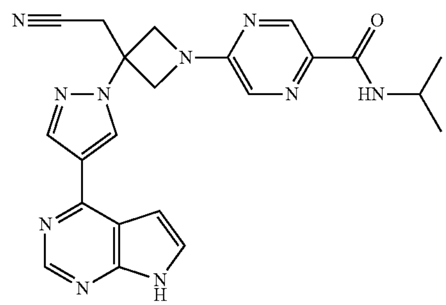 [SMILES: CC(C)NC(=O)c1cnc(N2CC(CC#N)(n3cc(-c4ncnc5[nH]ccc45)cn3)C2)cn1] | + | >10 |
| 16 | US 2013/ 0018034 (Example 28) | 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide | 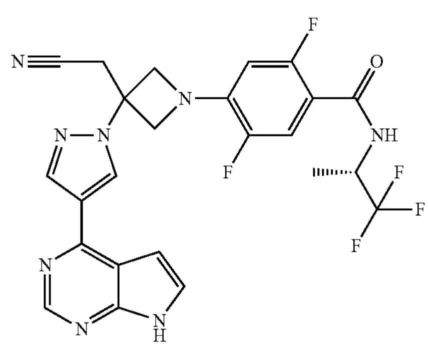 [SMILES: C[C@H](NC(=O)c1cc(F)c(N2CC(CC#N)(n3cc(-c4ncnc5[nH]ccc45)cn3)C2)cc1F)C(F)(F)F] | + | >10 |
| 17 | US 2013/ 0018034 (Example 34) | 5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide | 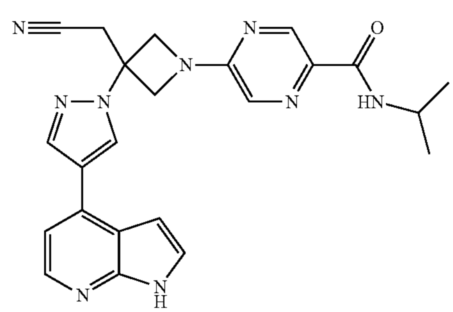 [SMILES: CC(C)NC(=O)c1cnc(N2CC(CC#N)(n3cc(-c4ccnc5[nH]ccc45)cn3)C2)cn1] | + | >10 |

TABLE 1-continued

| Comp. No. | Prep. | Name | Structure | JAK1 IC$_{50}$ (nM) | JAK2/ JAK1 |
|---|---|---|---|---|---|
| 18 | US 2013/ 0045963 (Example 45) | {1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile | 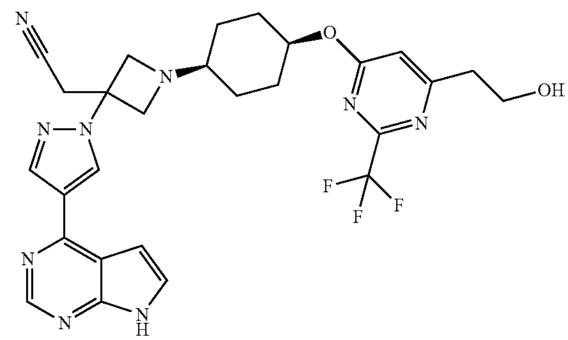 [SMILES: N#CCC1(n2cc(-c3ncnc4[nH]ccc34)cn2)CN([C@H]2CC[C@@H](Oc3cc(CCO)nc(C(F)(F)F)n3)CC2)C1] | + | >10 |
| 19 | US 2013/ 0045963 (Example 65) | {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 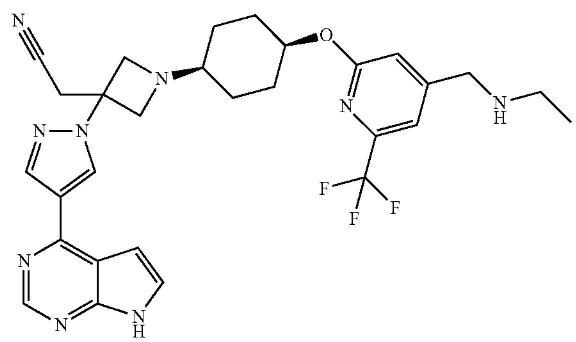 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] | + | >10 |
| 20 | US 2013/ 0045963 (Example 69) | {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 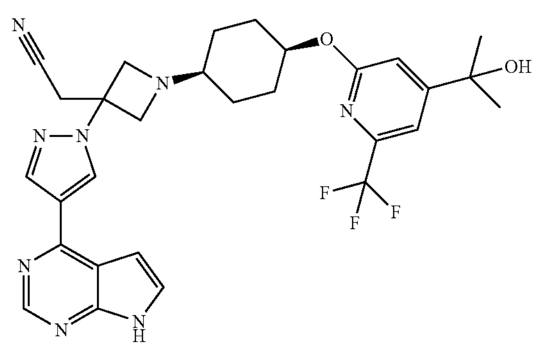 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] | + | >10 |
| 21 | US 2013/ 0045963 (Example 95) | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 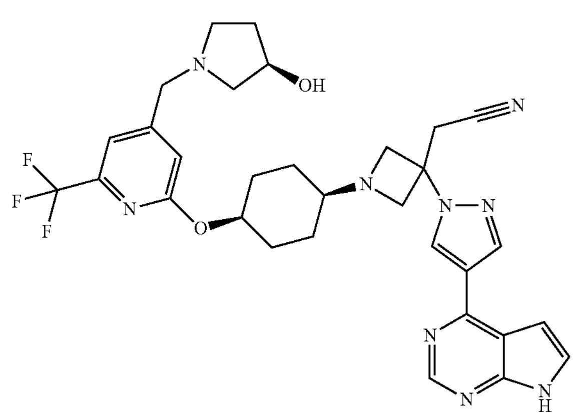 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 22 | US 2013/ 0045963 (Example 95) | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 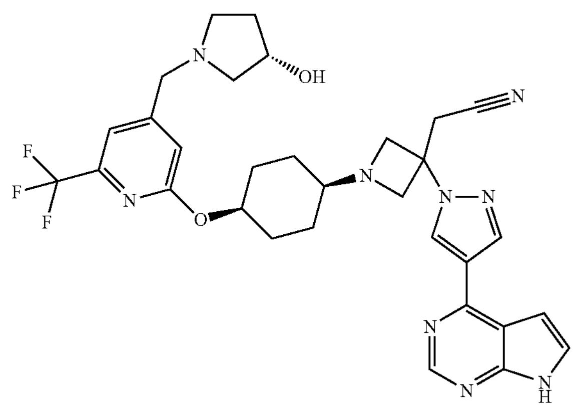 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] | + | >10 |
| 23 | US 2014/ 0005166 (Example 1) | {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 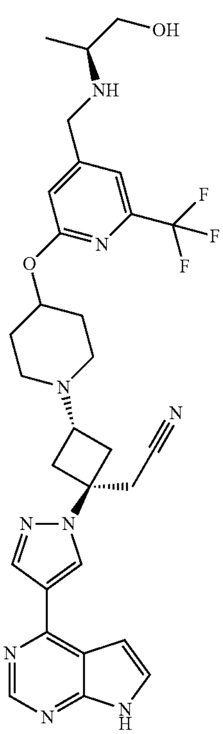 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] | + | >10 |

TABLE 1-continued

| Comp. No. | Prep. | Name | Structure | JAK1 IC$_{50}$ (nM) | JAK2/JAK1 |
|---|---|---|---|---|---|
| 24 | US 2014/0005166 (Example 14) | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 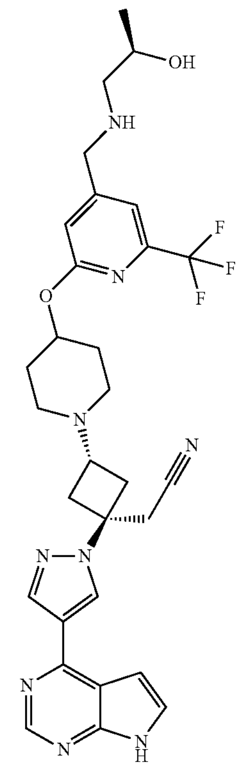 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |
| 25 | US 2014/0005166 (Example 15) | {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 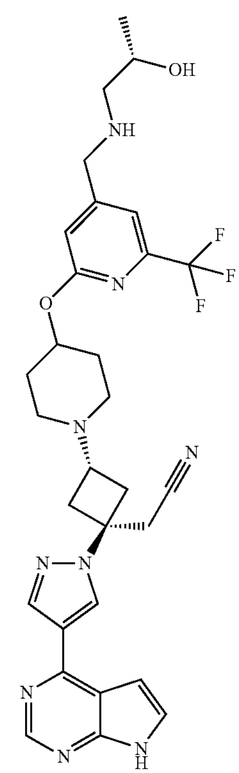 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |

TABLE 1-continued

| Comp. No. | Prep. | Name | Structure | JAK1 IC$_{50}$ (nM) | JAK2/ JAK1 |
|---|---|---|---|---|---|
| 26 | US 2014/ 0005166 (Example 20) | {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 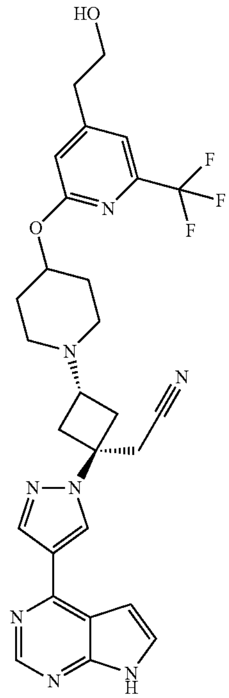 [SMILES: N#CC[C@]1(n2cc(-c3ncnc4[nH]ccc34)cn2)C[C@H](N2CCC(Oc3cc(CCO)cc(C(F)(F)F)n3)CC2)C1] | + | >10 |

+ means <10 nM (see Example A for assay conditions)
++ means ≤100 nM (see Example A for assay conditions)
+++ means ≤300 nM (see Example A for assay conditions)
$^a$Data for enantiomer 1
$^b$Data for enantiomer 2

In some embodiments, the JAK1 pathway inhibitor is {1-{1-[3-fluoro-2-(trifluoromethyl)isonicotinoyl]piperidin-4-yl}-3 [4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the JAK1 pathway inhibitor is {1-{1-[3-fluoro-2-(trifluoromethyl)i sonicotinoyl]piperidin-4-yl}-3[4-(7H-pyrrolo[2,3-d]pyrimidin-4-yl)-1H-pyrazol-1-yl]azetidin-3-yl}acetonitrile adipic acid salt.

The synthesis and preparation of {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile and the adipic acid salt of the same can be found, e.g., in US Patent Publ. No. 2011/0224190, filed Mar. 9, 2011, US Patent Publ. No. 2013/0060026, filed Sep. 6, 2012, and US Patent Publ. No. 2014/0256941, filed Mar. 5, 2014, each of which is incorporated herein by reference in its entirety.

In some embodiments, the JAK1 pathway inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the JAK1 pathway inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt.

The synthesis and preparation of 4-[3-(cyanomethyl)-3-(3',5'-dimethyl-1H,1'H-4,4'-bipyrazol-1-yl)azetidin-1-yl]-2, 5-difluoro-N-[(1S)-2,2,2-trifluoro-1-methylethyl]benzamide and the phosphoric acid salt of the same can be found, e.g., in US Patent Publ. No. 2014/0343030, filed May 16, 2014, which is incorporated herein by reference in its entirety.

In some embodiments, the JAK1 pathway inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In some embodiments, the JAK1 pathway inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile monohydrate.

Synthesis of ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile and characterization of the anhydrous and monohydrate forms of the same are described in US Patent Publ. No. 2014/0121198, filed Oct. 31, 2013 and US Patent Publ. No. 2015/0344497, filed Apr. 29, 2015, each of which is incorporated herein by reference in its entirety.

In some embodiments, the compounds of Table 1 are prepared by the synthetic procedures described in US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/

0045963, filed Aug. 17, 2012, and US Patent Publ. No. 2014/0005166, filed May 17, 2013, each of which is incorporated herein by reference in its entirety.

In some embodiments, JAK1 pathway inhibitor is selected from the compounds, or pharmaceutically acceptable salts thereof, of US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, the JAK1 pathway inhibitor is a compound of Formula I

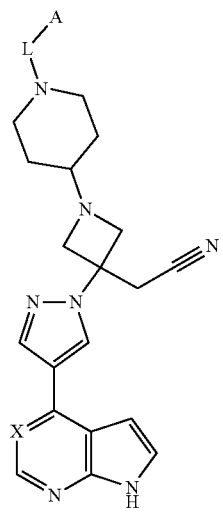

or a pharmaceutically acceptable salt thereof, wherein:

X is N or CH;

L is C(=O) or C(=O)NH;

A is phenyl, pyridinyl, or pyrimidinyl each of which is optionally substituted with 1 or 2 independently selected $R^1$ groups; and each $R^1$ is, independently, fluoro, or trifluoromethyl.

In some embodiments, the compound of Formula I is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the compound of Formula I is 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide, or a pharmaceutically acceptable salt thereof.

In some embodiments, the compound of Formula I is [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile, or a pharmaceutically acceptable salt thereof.

In some embodiments, the JAK1 pathway inhibitor is a compound of Formula II

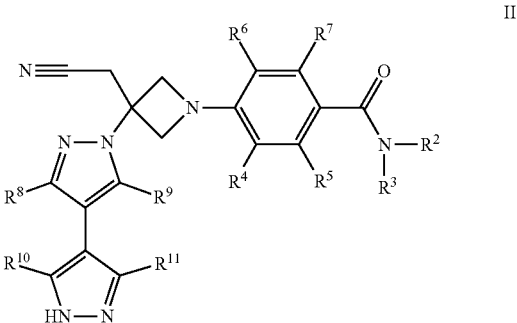

or a pharmaceutically acceptable salt thereof, wherein:

$R^2$ is $C_{1-6}$ alkyl, $C_{1-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl;

$R^3$ is H or methyl;

$R^4$ is H, F, or Cl;

$R^5$ is H or F;

$R^6$ is H or F;

$R^7$ is H or F;

$R^8$ is H or methyl;

$R^9$ is H or methyl;

$R^{10}$ is H or methyl; and $R^{11}$ is H or methyl.

In some embodiments, the compound of Formula II is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the JAK1 pathway inhibitor is a compound of Formula III

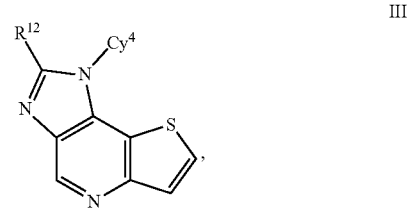

or a pharmaceutically acceptable salt thereof, wherein:

$Cy^4$ is a tetrahydro-2H-pyran ring, which is optionally substituted with 1 or 2 groups independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylaminosulfonyl, and $C_{1-3}$ alkylsulfonyl; and $R^{12}$ is —$CH_2$—OH, —CH($CH_3$)—OH, or —$CH_2$—$NHSO_2CH_3$.

In some embodiments, the compound of Formula III is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In some embodiments, the JAK1 pathway inhibitor, or a pharmaceutically acceptable salt thereof, is administered in a daily amount of from about 100 mg to about 600 mg on a free base basis. Accordingly, in some embodiments, the selective JAK1 pathway inhibitor is administered in a daily amount of about 100 mg, about 150 mg, about 200 mg, about 250 mg, about 300 mg, about 350 mg, about 400 mg, about 450 mg, about 500 mg, about 550 mg, or about 600 mg on a free base basis.

In some embodiments, the JAK1 pathway inhibitor, or a pharmaceutically acceptable salt thereof, is administered at a daily amount of about 200 mg on a free base basis.

In some embodiments, the JAK1 pathway inhibitor, or a pharmaceutically acceptable salt thereof, is administered at a daily amount of about 300 mg on a free base basis.

In some embodiments, the JAK1 pathway inhibitor, or a pharmaceutically acceptable salt thereof, is administered at a daily amount of about 400 mg on a free base basis.

In some embodiments, the JAK1 pathway inhibitor, or a pharmaceutically acceptable salt thereof, is administered at a daily amount of about 500 mg on a free base basis.

In some embodiments, the JAK1 pathway inhibitor, or a pharmaceutically acceptable salt thereof, is administered at a daily amount of about 600 mg on a free base basis.

In some embodiments, the JAK1 pathway inhibitor, or a pharmaceutically acceptable salt thereof, is administered once daily at an amount of about 200 mg on a free base basis.

In some embodiments, the JAK1 pathway inhibitor, or a pharmaceutically acceptable salt thereof, is administered once daily at an amount of about 300 mg on a free base basis.

In some embodiments, the JAK1 pathway inhibitor, or a pharmaceutically acceptable salt thereof, is administered once daily at an amount of about 400 mg on a free base basis.

In some embodiments, the JAK1 pathway inhibitor, or a pharmaceutically acceptable salt thereof, is administered once daily at an amount of about 500 mg on a free base basis.

In some embodiments, the JAK1 pathway inhibitor, or a pharmaceutically acceptable salt thereof, is administered once daily at an amount of about 600 mg on a free base basis.

In some embodiments, the JAK1 pathway inhibitor, or a pharmaceutically acceptable salt thereof, is administered as one or more sustained release dosage forms each comprising the JAK1 pathway inhibitor, or a pharmaceutically acceptable salt thereof.

Provided herein is a method for treating a cytokine-related disease or disorder in a subject in need thereof in a subject, comprising administering to the subject a daily dose of from about 100 mg to 600 mg on a free base basis of a JAK1 pathway inhibitor, or a pharmaceutically acceptable salt thereof, wherein the JAK1 pathway inhibitor, or a pharmaceutically acceptable salt thereof, is administered as one or more sustained release dosage forms comprising the JAK1 pathway inhibitor, or a pharmaceutically acceptable salt thereof.

The embodiments described herein are intended to be combined in any suitable combination as if the embodiments are multiply dependent claims (e.g., the embodiments related to the selective JAK1 pathway inhibitor and doses of the same, the embodiments related to any salt forms of the compounds disclosed herein, the embodiments related to the individual types of cytokine related diseases or disorders, and the embodiments related to composition and/or administration can be combined in any combination).

For example, provided herein is a method for treating a cytokine related disease or disorder selected from the group consisting of cytokine release syndrome (CRS), hemophagocytic lymphohistiocytosis (HLH), macrophage activation syndrome (MAS), or CAR-T-cell-related encephalopathy syndrome (CRES), in a subject, the method comprising administering to the subject a once-daily dose of about 200 mg on a free base basis of {1-{1-[3-fluoro-2-(trifluoromethyl)isonicotinoyl]piperidin-4-yl}-3-[4-(7H-pyrrolo[2,3-d]pyrimidin-4- yl)-1H-pyrazol-1-yl]azetidin-3-yl}acetonitrile, or a pharmaceutically acceptable salt thereof, wherein the dose comprises one or more sustained-release dosage forms each comprising the {1-{1-[3-fluoro-2-(trifluoromethyl)isonicotinoyl]piperidin-4-yl}-3-[4-(7H-pyrrolo[2,3-d]pyrimidin-4- yl)-1H-pyrazol-1-yl]azetidin-3-yl}acetonitrile, or a pharmaceutically acceptable salt thereof.

Sustained-release dosage forms of {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof (Table 1, Compound 1) can be found in US Publ. No. 2015/0065484, filed Aug. 6, 2014, which is hereby incorporated by reference in its entirety.

All possible combinations are not separately listed herein merely for the sake of brevity.

The compounds described herein can be asymmetric (e.g., having one or more stereocenters). All stereoisomers, such as enantiomers and diastereomers, are intended unless otherwise indicated. Compounds that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

In some embodiments, the compound has the (R)-configuration. In some embodiments, the compound has the (S)-configuration.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds described herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds described herein can also include isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formulae (I), (II), or (III) or a compound of Table 1 can be optionally substituted with deuterium atoms, such as —CD$_3$ being substituted for —CH$_3$). The term, "compound," as used herein is meant to include all stereoisomers, geometric isomers, tautomers, and isotopes of the structures depicted, unless the name indicates a specific stereoisomer. Compounds herein identified by name or structure as one particular tautomeric form are intended to include other tautomeric forms unless otherwise specified.

All compounds, and pharmaceutically acceptable salts thereof, can be found together with other substances such as water and solvents (e.g. hydrates and solvates) or can be isolated.

In some embodiments, the compounds described herein, or salts thereof, are substantially isolated. By "substantially isolated" is meant that the compound is at least partially or substantially separated from the environment in which it was formed or detected. Partial separation can include, for example, a composition enriched in the compounds described herein. Substantial separation can include compositions containing at least about 50%, at least about 60%, at least about 70%, at least about 80%, at least about 90%, at least about 95%, at least about 97%, or at least about 99% by weight of the compounds described herein, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

As used herein, the term "subject", "individual," or "patient," used interchangeably, refers to any animal, including mammals, preferably mice, rats, other rodents, rabbits, dogs, cats, swine, cattle, sheep, horses, or primates, and most preferably humans. In some embodiments, the "subject," "individual," or "patient" is in need of said treatment.

In some embodiments, the inhibitors are administered in a therapeutically effective amount. As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the dosage of the compound, or a pharmaceutically acceptable salt thereof, administered to a patient or individual is about 1 mg to about 2 g, about 1 mg to about 1000 mg, about 1 mg to about 500 mg, about 1 mg to about 200 mg, about 1 mg to about 100 mg, about 1 mg to 50 mg, or about 50 mg to about 500 mg. In some embodiments, the dosage of the compound, or a pharmaceutically acceptable salt thereof, is about 200 mg.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease; or (3) preventing the disease, condition or disorder in an individual who may be predisposed to the disease, condition or disorder but does not yet experience or display the pathology or symptomatology of the disease. In some embodiments, treating refers to inhibiting or ameliorating the disease. In some embodiments, treating is preventing the disease.

Combination Therapies

The methods described herein can further comprise administering one or more additional therapeutic agents. The one or more additional therapeutic agents can be administered to a patient simultaneously or sequentially.

In some embodiments, the additional therapeutic agent is an IL-6 antagonist or receptor antagonist. In some embodiments, the IL-6 receptor antagonist is tocilizumab.

In some embodiments, the additional therapeutic agent is an inhibitor of MCP-1. In some embodiments, the additional therapeutic agent is an inhibitor of MIP1B. In some embodiments, the additional therapeutic agent is an inhibitor of IL-2R. In some embodiments, the additional therapeutic agent is an inhibitor of IL-1R. In some embodiments, the additional therapeutic agent is an inhibitor of TNF-α.

In some embodiments, the additional therapeutic agent is an anti-CD25 antibody. In some embodiments, the anti-CD25 antibody is daclizumab.

In some embodiments, the additional therapeutic agent is an antagonist of IL-1β.

In some embodiments, the additional therapeutic agent is an IL1 receptor antagonist (IL1Ra). In some embodiments, the IL1 receptor antagonist (IL1Ra) is anakinra.

In some embodiments, the additional therapeutic agent is a corticosteroid. In some embodiments, the corticosteroid is prednisone.

In some embodiments, any of the preceding additional therapeutic agents is used in further combination with a corticosteroid (e.g., prednisone).

In some embodiments, the additional therapeutic agents comprise tocilizumab and a corticosteroid. In some embodiments, the additional therapeutic agents comprise tocilizumab and prednisone.

Pharmaceutical Formulations and Dosage Forms

When employed as pharmaceuticals, the JAK1 pathway inhibitors or pharmaceutically acceptable salts thereof, can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the JAK1 pathway inhibitor described herein, or a pharmaceutically acceptable salt thereof, in combination with one or more pharmaceutically acceptable carriers (excipients). In some embodiments, the composition is suitable for topical administration. In making the compositions, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The JAK1 pathway inhibitors may be milled using known milling procedures such as wet milling to obtain a particle size appropriate for tablet formation and for other formulation types. Finely divided (nanoparticulate) preparations of the JAK1 selective inhibitors can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the invention contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the invention contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the invention.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound described herein. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed herein.

Kits

The present invention also includes pharmaceutical kits useful, for example, in the treatment and/or prevention of cytokine-related diseases or disorders, such as CRS, which include one or more containers containing a pharmaceutical composition comprising a therapeutically effective amount of a compound described herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be JAK inhibitors according to at least one assay described herein.

Example A: In Vitro JAK Kinase Assay

JAK1 pathway inhibitors that can be used for the treatment of cytokine-related diseases or disorders are tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag are expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds are measured for each kinase in the 40 microL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions is 1 mM. Reactions are carried out at room temperature for 1 hour and then stopped with 20 µL 45 mM EDTA, 300 nM SA-APC, 6 nM Eu-Py20 in assay buffer (Perkin Elmer, Boston, MA). Binding to the Europium labeled antibody takes place for 40 minutes and HTRF signal was measured on a Fusion plate reader (Perkin Elmer, Boston, MA). The compounds in Table 1 were tested in this assay and shown to have the $IC_{50}$ values also found in Table 1.

Example B: Anti-CD3 Antibody-Induced Cytokine Release Syndrome in BALB/c Mice

JAK1 pathway inhibitors can be tested for efficacy against CRS according to an in vivo assay described in Ferran, C. et al. *Clin. Exp. Immunol.* 1991, 86, 537-543. Specifically, this study can test the ability of a compound to reduce or ameliorate anti-CD3 antibody-induced cytokine release syndrome (CRS) in BALB/c mice. The antibody, clone 145-2C11, is an immunoglobin G (IgG) hamster MoAb that is specific for the ε chain of the CD3 murine molecule (Léo, O. et al., *Proc. Natl. Acad. Sci. USA*, 1987, 34, 1374). Treatment with 145-2C11 induces high affinity IL-2 receptors at the surface of spleen T-cells and results in a release of some cytokines such as tumor necrosis factor (TNF-α), IL-2, IL-3, IL-6, and interferon-gamma (IFN-γ) (Ferran, et al. *Eur. J. Immunol.* 1990, 20, 509-515 and Algre, M. et al., *Eur. J. Immunol.*, 1990, 707). Release of these cytokines results in behavioral changes (e.g., inactivity, piloerection, etc) of the animals.

A. Materials and Methods

| | |
|---|---|
| Species/strain: | Mice: Male BALB/c |
| Physiological state: | Normal |
| Age/weight range at start of study: | 6-8 weeks old |
| Animal supplier: | Charles River Laboratories |
| Number/sex of animals: | 32 total Male mice |
| Randomization: | Mice will be randomized into four (4) groups of eight (8) mice prior to the commencement of the study. |
| Justification: | Injection of anti-CD3 antibody (clone 145-2C11) has been shown in the literature to induce cytokine release syndrome and serves as a model with which to test the efficacy of potential therapies. |
| Replacement | Animals will not be replaced during the course of the study. |

Anti-CD3ε

| | |
|---|---|
| Identity and lot number: | Anti-CD3ε Clone 145-2C11 |
| Source: | BioXCell |
| Storage conditions: | 4° C. |
| Vehicle: | Sterile saline |
| Dose: | 10 µg |
| Dosing Route/Volume | IV, 100 µL per animal |
| Compound: | Compound 1 (Jak1 inhibitor)[A] |
| Storage conditions: | RT (formulation RT on tube rotator) |
| Vehicle: | 0.5% Methylcellulose |
| Dose(s): | 60 mg/kg and 120 mg/kg |
| Dosing Route/Volume | PO, 0.1 mL/20 g (5 mL/kg) |
| Frequency and duration of dosing: | QD on day 0 |

[A]The synthesis and preparation of Compound 1 of Table 1 or {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile and the adipic acid salt of the same can be found, e.g., in US Patent Publ. No. 2011/0224190, filed Mar. 9, 2011, US Patent Publ. No. 2013/0060026, filed Sep. 6, 2012, and US Patent Publ. No. 2014/0256941, filed Mar. 5, 2014, each of which is incorporated herein by reference in its entirety.

B. Experimental Design

The main objective of this study was to test the ability of a JAK1 pathway inhibitor (e.g., Compound 1) to reduce or ameliorate anti-CD3 antibody-induced cytokine release syndrome (CRS) in BALB/c mice. A total of thirty-two (32) BALB/c mice were used for this one day study. Animals were weighed prior to test article dosing, and monitored for the duration of the experiment. On day 0, one hour (1) prior to anti-CD3 antibody administration, vehicle (0.5% methylcellulose) or Compound 1 were given in a single dose via oral gavage (PO) to animals in groups 2-4 as is detailed in Table 1A. Group 1 served as naïve controls and were not treated. Following the 1 hour pre-treatment with vehicle or Compound 1, animals in Groups 2-4 were administered 10 µg of an anti-CD3ε antibody (clone 145-2C11) via intravenous injection (IV) in order to induce CRS. All animals were euthanized via $CO_2$ inhalation 1.5 hours after anti-CD3 administration. Whole blood was collected via cardiac puncture into $K_2EDTA$ tubes and stored on ice until plasma processing occurred. Plasma was collected and stored at −80° C. until cytokine multiplex was performed.

TABLE 1A

Study Design

| Group | No. Animals | TA Pre-Treatment (PO) | Dosing schedule | Anti-CD3 (10 µg, IV) | Sacrifice Schedule/ Collection | Endpoints |
|---|---|---|---|---|---|---|
| 1 | 8/males | Naïve | 60 minutes before | – | 1.5 hr after anti-CD3 | Plasma collection for |
| 2 | 8/males | Vehicle | 60 minutes before | + | 1.5 hr after anti-CD3 | Plasma collection for |

TABLE 1A-continued

Study Design

| Group | No. Animals | TA Pre-Treatment (PO) | Dosing schedule | Anti-CD3 (10 μg, (IV) | Sacrifice Schedule/ Collection | Endpoints |
|---|---|---|---|---|---|---|
| 3 | 8/males | Compound 1 (60 mg/kg) | anti-CD3 | + | administration Whole blood via cardiac puncture (K$_2$EDTA tubes) | multiplex cytokine analysis |
| 4 | 8/males | Compound 1 (120 mg/kg) | | + | | |

C. Experimental Procedures

I. Test Article Pre-Treatment

On day 0, animals were dosed with vehicle or test articles or Compound 1 as shown in Table 1A. Group 2 received a single dose of vehicle (0.5% methylcellulose) via PO at 0.1 mL/20 g. Group 3 received a single dose of 60 mg/kg Compound 1 via PO at 0.1 mL/20 g. Group 4 received a single dose of 120 mg/kg Compound 1 via PO at 0.1 mL/20 g. Group 1 served as the naïve controls and were not treated.

II. Anti-CD3ε Antibody Administration

One (1) hour after test article administration, an anti-CD3ε antibody (clone 145-2C11) was administered via IV injection to Groups 2-4. Each animal in Groups 2-4 received 10 μg of anti-CD3ε antibody in 0.1 mL.

III. In-Life monitoring

After the administration of the anti-CD3 antibody, animals were closely monitored for signs of distress due to the resulting systemic inflammatory response. Animals that were unable to right themselves, cold to the touch, or moribund were euthanized. Moribund animals were euthanized by CO$_2$ inhalation, and blood was collected via cardiac puncture and plasma retained.

IV. Sacrifice

One and a half (1.5) hours after anti-CD3 antibody administration all animals were euthanized by CO$_2$ inhalation.

V. Collection of Samples

Upon sacrifice, whole blood was collected from each animal via cardiac puncture into K$_2$EDTA tubes. The blood was centrifuged and the plasma collected in cryovials. The plasma was frozen and stored at −80° C. for the downstream cytokine multiplex assay.

VI. Cytokine Multiplex Analysis

Plasma samples are thawed on ice and used for a cytokine multiplex according to the manufacturer's protocol (ThermoFisher).

D. Results

Figure 1:
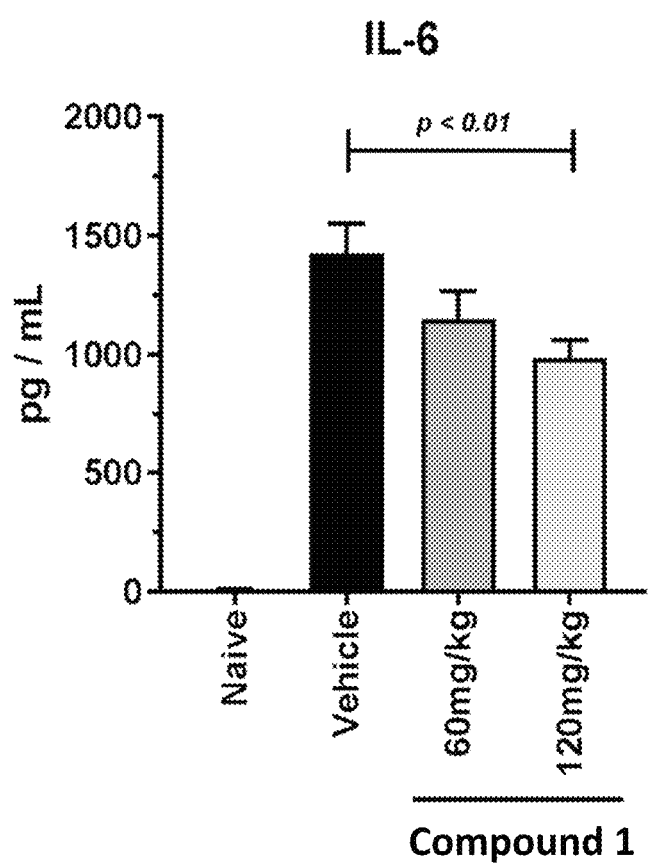
FIG. 1 depicts dose-dependent inhibition of the IL-6 concentrations upon administration of Compound 1 within the blood compartment during anti-CD3 antibody induced cytokine release syndrome (see Example B).

Compound 1 dose-dependently inhibited IL-6 concentrations within the blood compartment (FIG. 1). This serves as confirmation of the biological activity observed in the Con A preclinical model described below in Example C. An unpaired one-way analysis of variance (ANOVA) incorporating Sidak's multiple test comparison was performed using GraphPad Prism (version 4.00; GraphPad Software, San Diego California, USA). A value of p<0.05 was considered significant.

Example C: Concanavalin A Induced Cytokine Release Syndrome

Concanavalin A (Con A) is a selective T lymphocyte mitogen resulting in broad inflammatory cytokine release and proliferation of CD4 and CD8 T-cells. Injection of Con-A has been shown in the literature to induce cytokine release syndrome and serves as a model with which to test the efficacy of cytokine release syndrome therapies (Gantner, F. at al. *Hepatology*, 1995, 21, 190-198). The mitogen response is dependent on expression of the T-cell receptor. Animals exhibit behavioral changes such as fever, malaise, hypotension, hypoxia, capillary leak, and potential multi-organ toxicity.

A. Materials and Methods

| | |
|---|---|
| Species/strain: | Mice: Female BALB/c |
| Physiological state: | Normal |
| Age/weight range at start of study: | 6-8 weeks old |
| Animal supplier: | Taconic |
| Number/sex of animals: | 40 total mice |
| Randomization: | Mice were randomized into five (5) groups of eight (8) mice prior to the commencement of the study. |
| Justification: | Injection of Con-A has been shown in the literature to induce cytokine release syndrome and serves as a model with which to test the efficacy of potential therapies. |

B. Experimental Design

In particular, this study tests the ability of a selective JAK1 inhibitor (e.g., Compound 1, Table 1) to reduce or ameliorate Con A-induced cytokine release syndrome (CRS) in BALB/c mice. A total of forty (40) BALB/c mice were used for this one day study. Animals were weighed prior to test article dosing, and monitored for the duration of the experiment. On day 0, Sixty (60) minutes prior to Con A administration, vehicle (0.5% methylcellulose) or Compound 1 (60 and 120 mg/kg) was given in a single dose via oral gavage (PO) to animals in groups 2-4 as detailed in Table 2A. Group 1 served as naïve controls and were not treated. Following the 45 minutes pre-treatment with vehicle or Compound 1, animals in Groups 2-4 were administered 20 mg/kg of Con A via intravenous injection (IV) in order to induce CRS. All animals were euthanized via CO$_2$ inhalation two hours after Con A administration. Whole blood was collected via cardiac puncture into K$_2$EDTA tubes and stored on ice until plasma processing occurs. Plasma was collected and stored at −80° C. until cytokine multiplex was performed.

TABLE 2A

Study Design

| Group | No. of Animals | Pre-Treatment (PO) | Dosing schedule | Con-A (IV) | Sacrifice Schedule/ Collection | Endpoints |
|---|---|---|---|---|---|---|
| 1 | 10 | Naïve | | − | 2 h after Con A administration Whole blood via cardiac puncture | Plasma collection for multiplex cytokine analysis |
| 2 | 10 | Vehicle | 60 minutes before Con A | + | | |
| 3 | 10 | Compound 1 (60 mg/kg) | | + | | |
| 4 | 10 | Compound 1 (120 mg/kg) | | + | | |

C. Experimental Procedures

Day −1

Animals were weighed and Con-A dose (20 mg/kg) calculated. Vehicle and Compound 1 were prepared at corresponding doses.

Day 0
I. Test Article Pre-Treatment

On day 0, animals were dosed with vehicle or Compound 1, as in Table 2A. Group 1 served as the naive controls and were not treated. Group 2 received a single dose of vehicle (0.5% methylcellulose) via PO at 0.1 mL/20 g. Group 3 received a single dose of 60 mg/kg Compound 1 via PO at 0.1 mL/20 g. Group 4 received a single dose of 120 mg/kg Compound 1 via PO at 0.1 mL/20 g.

II. Con-A Administration

Sixty (60) minutes after test article administration, Con-A was administered via IV injection to Groups 2-4. Each animal in Groups 2-4 received 20 mg/kg of Con-A in 0.2 mL.

III. In-Life monitoring

After the administration of Con-A, animals were closely monitored for signs of distress due to the resulting systemic inflammatory response.

IV. Sacrifice

Two hours after Con-A administration all animals were euthanized by $CO_2$ inhalation.

V. Collection of Samples

Upon sacrifice, whole blood was collected from each animal via cardiac puncture into $K_2$EDTA tubes. The blood was centrifuged and the plasma collected in cryovials. The plasma was frozen and stored at −80° C. for the downstream cytokine multiplex assay.

VI. Cytokine Multiplex Analysis

Plasma samples are thawed on ice and used for a cytokine multiplex according to the manufacturer's protocol (ThermoFisher).

D. Results

Figure 2A:
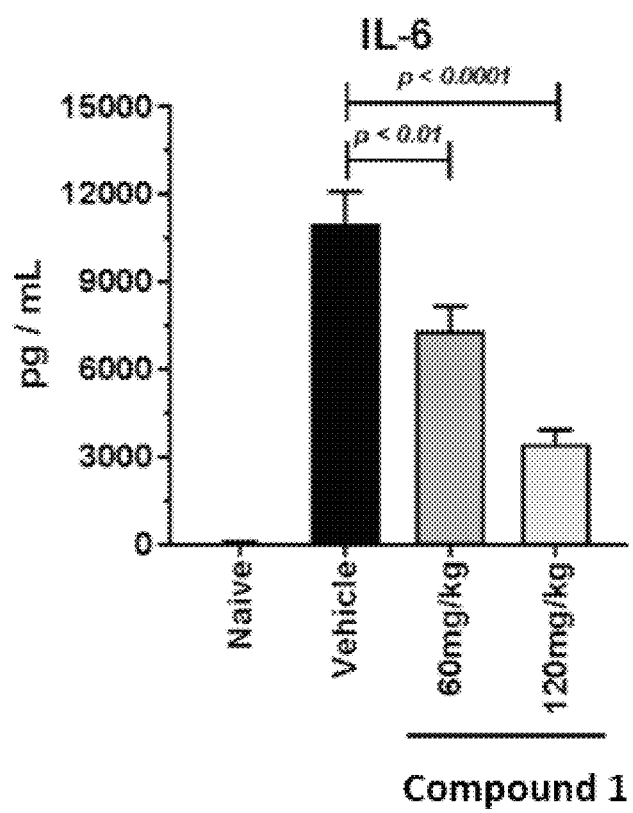
FIGS. 2A-2C depict dose dependent inhibition of T-cell derived cytokines (i.e., IL-6, IFNγ, and GM-CSF) upon administration of Compound 1 during concanavalin A induced cytokine release syndrome (see Example C).
Figure 2B:
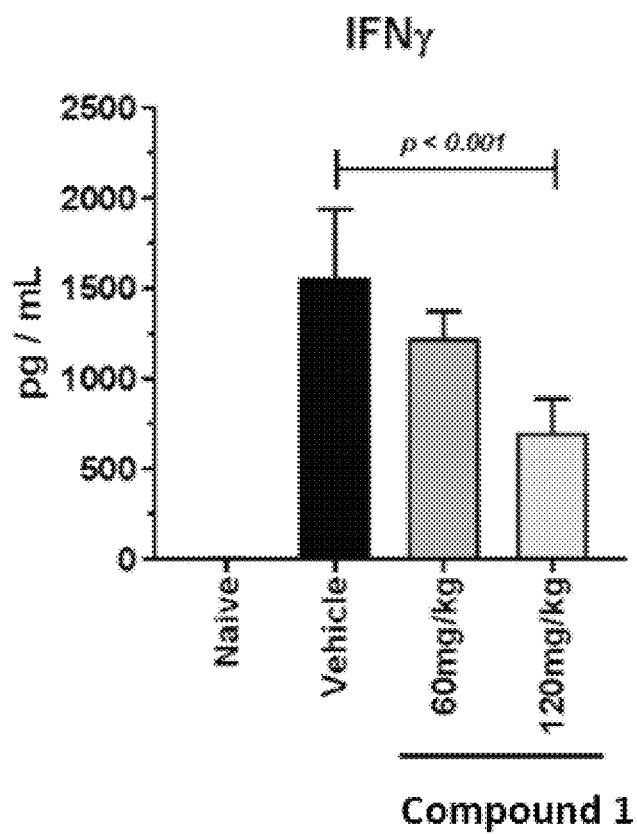
Figure 2C:
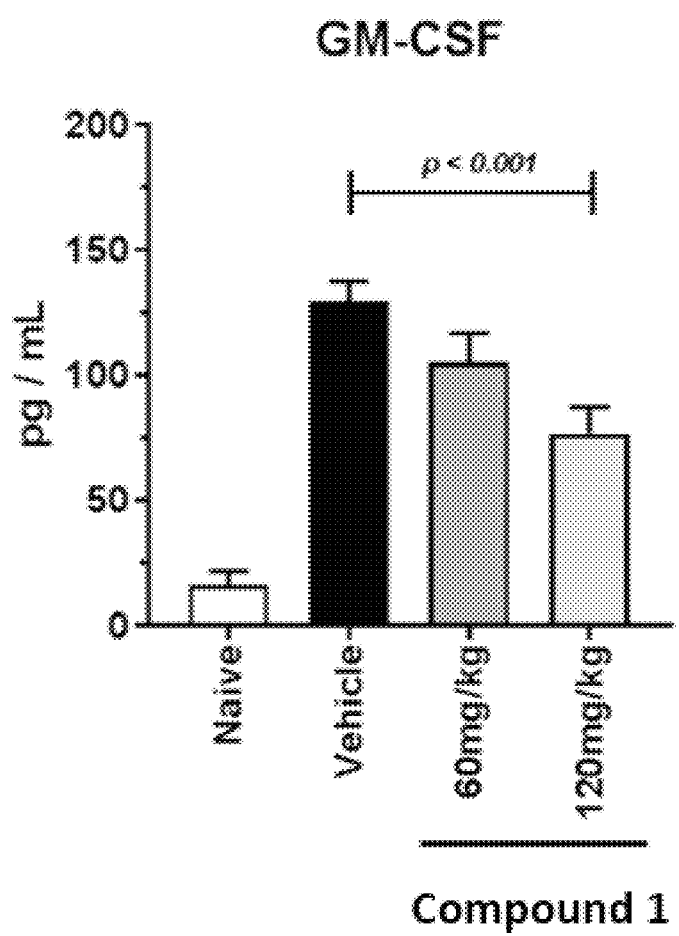
Figure 3A:
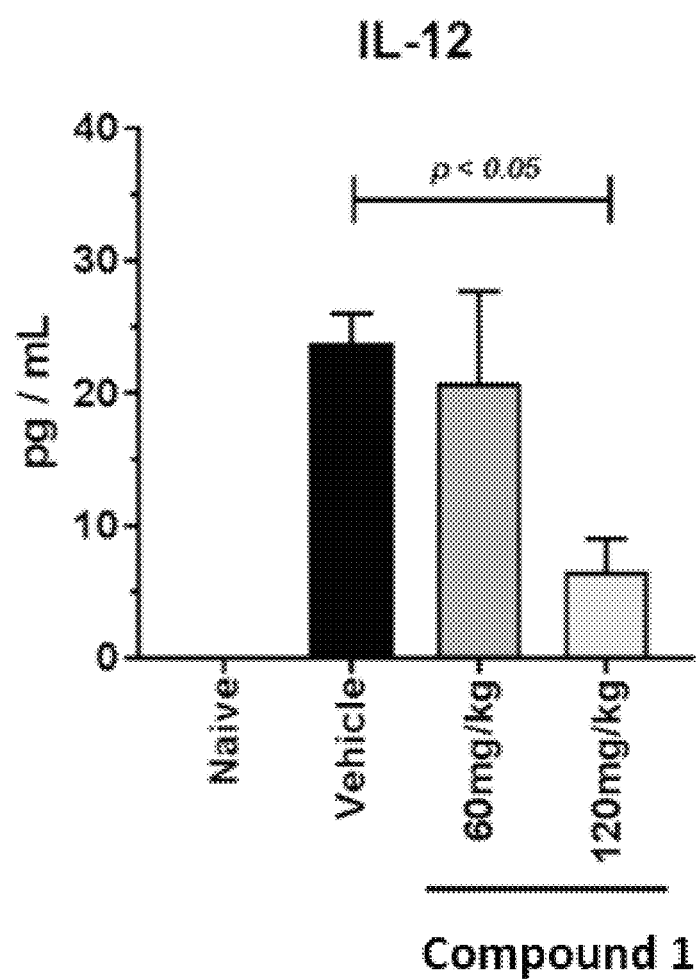
FIGS. 3A-3C depict dose dependent inhibition of monocyte and/or macrophage derived cytokines (i.e., IL-12, IL-1β, and IL-18) upon administration of Compound 1 during concanavalin A induced cytokine release syndrome (see Example C).
Figure 3B:
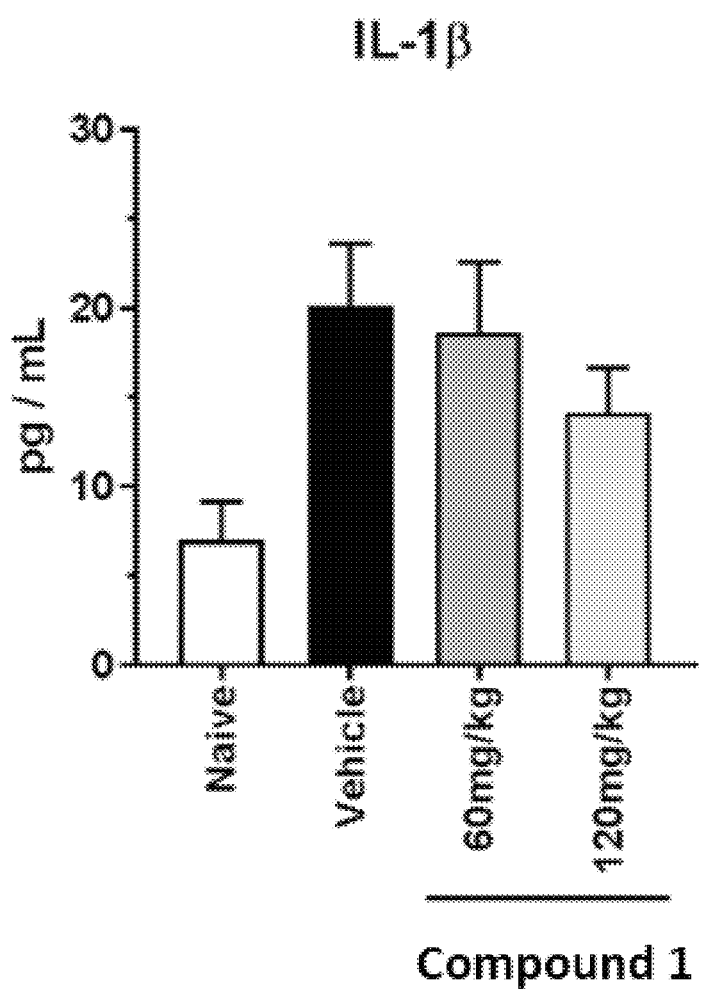
Figure 3C:
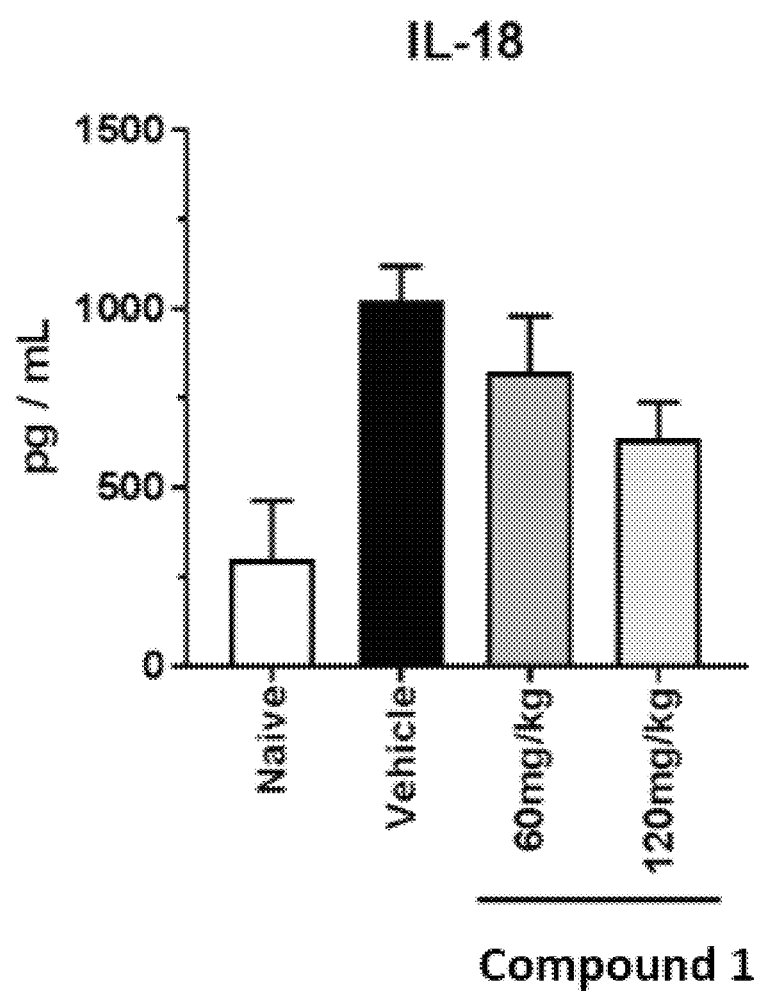

Compound 1 dose-dependently inhibited IL-6 concentrations within the blood compartment (FIG. 2A). This cytokine is a key mediated of CRS pathophysiology. The T-cell derived IFNγ and GM-CSF cytokines were also significantly inhibited suggesting that Compound 1 has therapeutic potential beyond tocilizumab's restricted mechanism of action (anti-IL-6R only) (FIGS. 2B and 2C).

Monocytes and/or macrophage derived cytokines were also reduced. Statistically significant dose-dependent IL-12 reduction (FIG. 3A) was observed as well as trends for treatment effect with IL-1β (FIG. 3B) and IL-18 (FIG. 3C) suggesting that JAK1 specific inhibition has therapeutic potential across immune cell types implicated in CRS pathology.

Importantly, the cytokine IL-5 (FIG. 4) was unaffected by Compound 1 treatment, is JAK1 independent and not implicated in CRS pathology. This data suggests that Compound 1 based efficacy is not mediated via broad, non-specific, immune suppression.

An unpaired one-way analysis of variance (ANOVA) incorporating Sidak's multiple test comparison was performed using GraphPad Prism (version 4.00; GraphPad Software, San Diego California, USA). A value of $p<0.05$ was considered significant.

Example D: Preparation of Sustained Release Formulations of Compound 1

Sustained release tablets comprising Compound 1 were prepared with the excipients being in the amounts shown in the tables below. Protocol A was used for the SR1 tablets, Protocol B was used for the SR2 tablets, Protocol C was used for the SR3 tablets and the 25 mg SR tablets, and Protocol D was used for the SR4 tablets. These procedures are disclosed in US Patent Publ. No. 2015/0065484, which is directed to sustained release dosage forms of Compound 1.

Protocol A:
Step 1. Individually screen the adipic acid salt of Compound 1, microcrystalline cellulose, hypromelloses (Methocel K100 LV and Methocel K4M), and lactose monohydrate.
Step 2. Transfer the screened material from Step 1 to a suitable blender and mix.
Step 3. Transfer the blend from Step 2 to a suitable granulator and mix.
Step 4. Add purified water while mixing.
Step 5. Transfer the granules from Step 4 into a suitable dryer and dry until LOD is less than 3%.
Step 6. Screen the granules from Step 5.
Step 7. Mix screened Magnesium Stearate with granules in Step 6 in a suitable blender.
Step 8. Compress the final blend in Step 7 on a suitable rotary tablet press.

Protocol B:
Step 1. Individually screen the adipic acid salt of Compound 1, microcrystalline cellulose, hypromellose and pregelatinized starch.
Step 2. Transfer the screened material from Step 1 to a suitable blender and mix.
Step 3. Transfer the blend from Step 2 to a suitable granulator and mix.
Step 4. Add purified water while mixing.
Step 5. Transfer the granules from Step 4 into a suitable dryer and dry until LOD is less than 3%.
Step 6. Screen the granules from Step 5.
Step 7. Individually screened polyox, butylated hydroxytoluene and colloidal silicone dioxide.
Step 8. Transfer the granules from Step 6 and material from Step 7 into a suitable blender and mix.
Step 9. Add screened Magnesium Stearate to the material in Step 8 and continue blending.
Step 10. Compress the final blend in Step 9 on a suitable rotary tablet press.

Protocol C:
Step 1. Individually screen lactose monohydrate, the adipic acid salt of Compound 1, microcrystalline cellulose and hypromelloses through a suitable screen.
Step 2. Transfer the screened material from Step 1 to a suitable blender and mix.
Step 3. Transfer the blend from Step 2 to a suitable granulator and mix.
Step 4. Add purified water while mixing.
Step 5. Screen wet granules through a suitable screen.
Step 6. Transfer the granules from Step 5 into a suitable dryer and dry until LOD is less than 3%.
Step 7. Mill the granules from Step 6.
Step 8. Mix screened magnesium stearate with granules in Step 7 in a suitable blender.
Step 9. Compress the final blend in Step 8 on a suitable rotary tablet press.

Protocol D:
Step 1. Individually screen pregelatinized starch, the adipic acid salt of Compound 1, hypromellose, and a portion of required microcrystalline cellulose through a suitable screen.
Step 2. Transfer the screened material from Step 1 to a suitable blender and mix.
Step 3. Transfer the blend from Step 2 to a suitable granulator and mix.
Step 4. Add purified water while mixing.

Step 5. Screen wet granules through a suitable screen.

Step 6. Transfer the granules from Step 5 into a suitable dryer and dry until LOD is less than 3%.

Step 7. Mill the granules from Step 6.

Step 8. Screen the remaining portion of microcrystalline cellulose and half of the sodium bicarbonate.

Step 9. Transfer the milled granules from Step 7 and screened materials from Step 8 into a suitable blender and mix.

Step 10. Screen the remaining portion of sodium bicarbonate and mix with blend in Step 9.

Step 11. Screen magnesium stearate and mix with blend in Step 10.

Step 12. Compress the final blend in Step 11 on a suitable rotary tablet press.

SR1: Composition of 100 mg Sustained Release Tablets

| Component | Function | Weight (mg/tablet) | Composition (wt %) |
|---|---|---|---|
| Adipic acid salt of Compound 1[a] | Active | 126.42[a] | 21.1 |
| Microcrystalline Cellulose | Filler | 60.0 | 10.0 |
| Hypromellose (Methocel K100LV) | Release Control | 60.0 | 10.0 |
| Hypromellose (Methocel K4M) | Release Control | 60.0 | 10.0 |
| Lactose Monohydrate | Filler | 290.58 | 48.4 |
| Magnesium Stearate[b] | Lubricant | 3.0 | 0.5 |
| Purified Water[c] | Granulating Liquid | q.s. | — |
| Total | | 600.0 | 100 |

[a] Conversion factor for adipate salt to free base is 0.7911
[b] Added after granulation
[c] Removed during processing SR2: Composition of 100 mg Sustained Release Tablets

| Component | Function | Weight (mg/tablet) | Composition (wt %) |
|---|---|---|---|
| Adipic acid salt of Compound 1[a] | Active | 126.4[a] | 21.1 |
| Microcrystalline Cellulose | Filler | 180.0 | 30.0 |
| Hypromellose (Methocel K100LV) | Binder | 6.0 | 1.0 |
| Polyethylene Oxide (Polyox WRS 1105)[b] | Release Control | 180.0 | 30.0 |
| Pregelatinized Starch | Filler | 101.6 | 16.9 |
| Colloidal Silicon Dioxide[b] | Glidant | 3.0 | 0.5 |
| Butylated Hydroxytoluene[b] | Antioxidant | 0.012 | 0.002 |
| Magnesium Stearate[b] | Lubricant | 3.0 | 0.5 |
| Purified Water[c] | Granulating Liquid | q.s. | — |
| Total | | 600.0 | 100.0 |

[a] Conversion factor for adipate salt to free base is 0.7911
[b] Added after granulation
[c] Removed during processing SR3 (100 mg): Composition of 100 mg Sustained Release Tablets

| Component | Function | Weight (mg/tablet) | Composition (wt %) |
|---|---|---|---|
| Adipic acid salt of Compound 1[a] | Active | 126.4[a] | 21.1 |
| Microcrystalline Cellulose | Filler | 108.0 | 18.0 |
| Hypromellose (Methocel K100LV) | Release Control | 42.0 | 7.0 |
| Hypromellose (Methocel K4M) | Release Control | 30.0 | 5.0 |
| Lactose Monohydrate | Filler | 290.6 | 48.4 |
| Magnesium Stearate[b] | Lubricant | 3.0 | 0.5 |
| Purified Water[c] | Granulating Liquid | q.s. | — |
| Total | | 600.0 | 100.0 |

[a] Conversion factor for adipate salt to free base is 0.7911
[b] Added after granulation
[c] Removed during processing SR4: Composition of 100 mg Sustained Release Tablets

| Excipient | Function | Weight (mg/tablet) | Composition (wt %) |
|---|---|---|---|
| Adipic acid salt of Compound 1[a] | Active | 126.4[a] | 21.1 |
| Microcrystalline Cellulose[d] | Filler | 104.6 | 17.4 |
| Hypromellose (Methocel K100LV) | Release Control | 210.0 | 35.0 |
| Pregelatinized Starch | Filler | 60.0 | 10.0 |
| Sodium Bicarbonate[b] | Gastric Floating Aid | 96.0 | 16.0 |
| Magnesium Stearate[b] | Lubricant | 3.0 | 0.5 |
| Purified Water[c] | Granulation Liquid | q.s. | — |
| Total | | 600.0 | 100.0 |

[a] Conversion factor for adipate salt to free base is 0.7911
[b] Added after granulation
[c] Removed during processing
[d] Partial added before and partial added after granulation 25 mg SR: Composition of 25 mg Sustained Release Tablets

| Component | Function | Weight (mg/tablet) | Composition (wt %) |
|---|---|---|---|
| Adipic acid salt of Compound 1[a] | Active | 31.6[a] | 12.6 |
| Microcrystalline Cellulose | Filler | 105.0 | 42.0 |
| Hypromellose, (Methocel K100LV) | Release Control | 25.0 | 10.0 |
| Hypromellose, (Methocel K4M) | Release Control | 25.0 | 10.0 |
| Lactose Monohydrate | Filler | 62.15 | 24.9 |
| Magnesium Stearate[b] | Lubricant | 1.25 | 0.5 |
| Purified Water[c] | Granulating Liquid | q.s. | — |
| Total | | 250 | 100.0 |

[a] Conversion factor for adipate salt to free base is 0.7911
[b] Added after granulation
[c] Removed during processing Various modifications of the invention, in addition to those described herein, will be apparent to those skilled in the art from the foregoing description. Such modifications

What is claimed is:

1. A method for treating a cytokine-related disease or disorder in a subject, said method comprising administering to the subject a JAK1 selective pathway inhibitor which is {1-{1-[3-fluoro-2-(trifluoromethyl)isonicotinoyl]piperidin-4-yl}-3-[4-(7H-pyrrolo [2,3-d]pyrimidin-4-yl)-1H-pyrazol-1-yl] azetidin-3-yl} acetonitrile, or a pharmaceutically acceptable salt thereof,
wherein the cytokine-related disease or disorder is hemophagocytic lymphohistiocytosis (HLH), macrophage activation syndrome (MAS), or CAR-T-cell-related encephalopathy syndrome (CRES).

2. The method of claim 1, wherein the cytokine-related disease or disorder is hemophagocytic lymphohistiocytosis (HLH).

3. The method of claim 1, wherein the cytokine-related disease or disorder is macrophage activation syndrome (MAS).

4. The method of claim 3, wherein the macrophage activation syndrome (MAS) is associated with systemic juvenile idiopathic arthritis.

5. The method of claim 1, wherein the cytokine-related disease or disorder is CAR-T-cell-related encephalopathy syndrome (CRES).

6. The method of claim 1, wherein the JAK1 selective pathway inhibitor is {1-{1-[3-fluoro-2-(trifluoromethyl) isonicotinoyl]piperidin-4-yl}-3-[4-(7H -pyrrolo [2,3-d]pyrimidin-4-yl)-1H-pyrazol-1-yl]azetidin-3-yl}acetonitrile adipic acid salt.

7. The method of claim 1, further comprising administering tocilizumab to said subject.

8. The method of claim 1, further comprising administering a corticosteroid to said subject.

9. The method of claim 1, further comprising administering prednisone to said subject.

10. The method of claim 1, further comprising administering tocilizumab and a corticosteroid to said subject.

11. The method of claim 2, wherein the JAK1 selective pathway inhibitor is {1-{1-[3-fluoro-2-(trifluoromethyl) isonicotinoyl]piperidin-4-yl}-3-[4-(7H -pyrrolo [2,3-d]pyrimidin-4-yl)-1H-pyrazol-1-yl]azetidin-3-yl}acetonitrile adipic acid salt.

12. The method of claim 3, wherein the JAK1 selective pathway inhibitor is {1-{1-[3-fluoro-2-(trifluoromethyl) isonicotinoyl]piperidin-4-yl}-3-[4-(7H -pyrrolo [2,3-d]pyrimidin-4-yl)-1H-pyrazol-1-yl]azetidin-3-yl}acetonitrile adipic acid salt.

13. The method of claim 4, wherein the JAK1 selective pathway inhibitor is {1-{1-[3-fluoro-2-(trifluoromethyl) isonicotinoyl]piperidin-4-yl}-3-[4-(7H -pyrrolo [2,3-d]pyrimidin-4-yl)-1H-pyrazol-1-yl]azetidin-3-yl}acetonitrile adipic acid salt.

14. The method of claim 5, wherein the JAK1 selective pathway inhibitor is {1-{1-[3-fluoro-2-(trifluoromethyl) isonicotinoyl]piperidin-4-yl}-3-[4-(7H -pyrrolo [2,3-d]pyrimidin-4-yl)-1H-pyrazol-1-yl]azetidin-3-yl} acetonitrile adipic acid salt.

15. The method of claim 1, wherein the treating comprises ameliorating or inhibiting the cytokine-related disease or disorder in the subject.

16. A method for treating a cytokine-related disease or disorder in a subject, said method comprising administering to the subject a monotherapy which is {1-{1-[3-fluoro-2-(trifluoromethyl) isonicotinoyl]piperidin-4-yl}-3-[4-(7H-pyrrolo [2,3-d]pyrimidin-4-yl)-1H-pyrazol-1-yl]azetidin-3-yl}acetonitrile, or a pharmaceutically acceptable salt thereof,
wherein the cytokine-related disease or disorder is hemophagocytic lymphohistiocytosis (HLH), macrophage activation syndrome (MAS), or CAR-T-cell-related encephalopathy syndrome (CRES).

17. The method of claim 16, wherein the cytokine-related disease or disorder is hemophagocytic lymphohistiocytosis (HLH).

18. The method of claim 16, wherein the cytokine-related disease or disorder is macrophage activation syndrome (MAS).

19. The method of claim 18, wherein the macrophage activation syndrome (MAS) is associated with systemic juvenile idiopathic arthritis.

20. The method of claim 16, wherein the cytokine-related disease or disorder is CAR-T-cell-related encephalopathy syndrome (CRES).

21. The method of claim 16, wherein the treating comprises ameliorating or inhibiting the cytokine-related disease or disorder in the subject.

22. The method of claim 16, wherein the monotherapy is {1-{1-[3-fluoro-2-(trifluoromethyl) isonicotinoyl]piperidin-4-yl}-3-[4-(7H-pyrrolo [2,3-d]pyrimidin-4-yl)-1H-pyrazol-1-yl]azetidin-3-yl}acetonitrile adipic acid salt.

23. The method of claim 1, wherein the treating comprises preventing.

24. The method of claim 16, wherein the treating comprises preventing.

* * * * *